US011220717B2

(12) United States Patent
Penn-Nicholson et al.

(10) Patent No.: US 11,220,717 B2
(45) Date of Patent: Jan. 11, 2022

(54) BIOMARKERS FOR PROSPECTIVE DETERMINATION OF RISK FOR DEVELOPMENT OF ACTIVE TUBERCULOSIS

(71) Applicants: UNIVERSITY OF CAPE TOWN, Cape Town (ZA); Seattle Children's Hospital, Seattle, WA (US)

(72) Inventors: Adam Garth Penn-Nicholson, Cape Town (ZA); Thomas Jens Scriba, Cape Town (ZA); Alan Arnold Aderem, Seattle, WA (US); Daniel Edward Zak, Seattle, WA (US); Ethan Greene Thompson, Seattle, WA (US); Willem Albert Hanekom, Cape Town (ZA)

(73) Assignees: Seattle Children's Hospital, Seattle, WA (US); University of Cape Town, Cape Town (ZA)

( * ) Notice: Subject to any disclaimer, the term of this patent is extended or adjusted under 35 U.S.C. 154(b) by 385 days.

(21) Appl. No.: 15/775,323

(22) PCT Filed: Nov. 9, 2016

(86) PCT No.: PCT/IB2016/056737
§ 371 (c)(1),
(2) Date: May 10, 2018

(87) PCT Pub. No.: WO2017/081618
PCT Pub. Date: May 18, 2017

(65) Prior Publication Data
US 2019/0249228 A1  Aug. 15, 2019

(30) Foreign Application Priority Data
Nov. 11, 2015 (GB) ..................................... 1519872

(51) Int. Cl.
| | |
|---|---|
| *C12Q 1/68* | (2018.01) |
| *C12Q 1/689* | (2018.01) |
| *C12Q 1/6883* | (2018.01) |
| *C12Q 1/6851* | (2018.01) |
| *C12Q 1/686* | (2018.01) |

(52) U.S. Cl.
CPC ............ *C12Q 1/689* (2013.01); *C12Q 1/686* (2013.01); *C12Q 1/6851* (2013.01); *C12Q 1/6883* (2013.01); *C12Q 2600/106* (2013.01); *C12Q 2600/112* (2013.01); *C12Q 2600/158* (2013.01)

(58) Field of Classification Search
None
See application file for complete search history.

(56) References Cited

U.S. PATENT DOCUMENTS

| 9,476,099 B2 * | 10/2016 | Spinella ............... A61K 33/243 |
| 2011/0129817 A1 | 6/2011 | Banchereau et al. |
| 2014/0329704 A1 * | 11/2014 | Melton ................ C12Q 1/6881 |
| | | 506/9 |

FOREIGN PATENT DOCUMENTS

| WO | WO-2005003299 A2 * | 1/2005 | ............ C07K 14/47 |
| WO | 2013/155460 A1 | 10/2013 | |

OTHER PUBLICATIONS

International Search Report dated May 22, 2017, issued in corresponding International Application No. PCT/IB2016/056737, filed Nov. 9, 2016, 8 pages.
AB Applied Biosystems, "Gene Expression Assay Performance Guaranteed With the TaqMan® Assays QPCR Guarantee Program," White Paper, TaqMan® Assays QPCR Guarantee Program, Oct. 2010, <http://tools.thermofisher.com/content/sfs/manuals/cms041280.pdf> [retrieved May 10, 2018], 6 pages.
Written Opinion of the International Searching Authority dated May 18, 2017, issued in corresponding International Application No. PCT/IB2016/056737, filed Nov. 9, 2016, 13 pages.
Written Opinion (Replacement) of the International Searching Authority dated May 22, 2017, issued in corresponding International Application No. PCT/US2016/031383, filed Nov. 9, 2016, 18 pages.

* cited by examiner

*Primary Examiner* — Stephanie K Mummert
(74) *Attorney, Agent, or Firm* — Christensen O'Connor Johnson Kindness PLLC

(57) ABSTRACT

This invention relates to a prognostic method for determining the risk of an asymptomatic human subject with latent tuberculosis (TB) infection or apparent latent TB infection and/or after suspected exposure to TB progressing to active tuberculosis disease comprising the steps of quantifying and computationally analysing relative abundances of a collection of pairs of gene products ("TB biomarkers") derived from a sample obtained from the subject. The invention further relates to a collection of TB biomarkers that generates a transcriptomic signature of risk for prediction of the likelihood of an asymptomatic human subject with latent TB infection and/or after suspected exposure to TB progressing to active tuberculosis disease. Furthermore, a kit comprising gene-specific primers or oligonucleotide probes for the detection of pairs of TB biomarkers that generates a prognostic signature of risk for use with the method of the invention is described. In addition, the invention relates to a method of preventive treatment or prophylaxis for TB infection comprising the use of the prognostic method and/or the kit of the invention to select an appropriate or experimental treatment regime or intervention for the human subject and/or to monitor the response of the human subject to the TB prophylaxis.

2 Claims, 3 Drawing Sheets
Specification includes a Sequence Listing.

SEQUENCE LISTING

<160> NUMBER OF SEQ ID NOS: 4

<210> SEQ ID NO 1
<211> LENGTH: 568
<212> TYPE: DNA
<213> ORGANISM: Homo sapiens
<220> FEATURE:
<221> NAME/KEY: prim_transcript
<222> LOCATION: (1)..(568)

<400> SEQUENCE: 1

```
aaccgggtga acatgaccta cgagaagatg tctcgtgccc tgcgccacta ttataagctt    60
aatatcatta agaaggaacc ggggcagaaa ctcctgttca gaaatggact tcagctgatc   120
ttcatattca tatggagttt ccagtgaccc caaatagcca aaacagtctt ggaaagaaaa   180
acaaagttgg aggacccaca cttcctgatt ttgaaacttg ctacaaagct atagtactca   240
acaaagattg gtaatggcat aaggatatag attaagaaca gttttttcaa caaatagtgt   300
tgggacaatg ggtgtccaca tgcaaaagaa taaagttgtc cccttacctt acaccatctc   360 caaaattaa ctcaaaatat gtcaaagaca taaacgtaag agctaaaact gtaaaactcc   420
tagaataaaa cataggagta aatcttcatg accttggatt aggccattgt gtcttaaata   480
taacaccaaa agaataagta ataaaaaaat agataaattg aactccatca aaattaaaag   540
cctttgtgct tcataggaca ccatcaag                                      568
```

<210> SEQ ID NO 2
<211> LENGTH: 446
<212> TYPE: DNA
<213> ORGANISM: Homo sapiens
<220> FEATURE:
<221> NAME/KEY: prim_transcript
<222> LOCATION: (1)..(446)

<400> SEQUENCE: 2

```
ctatgtgaca gagctgacac atagaatccg atcaaaatcc tcacctgatg agaatgagaa    60
tgaggttgag gattcagctg actttgtgag cttcttccca gactttgtgt ggacactgag   120
agatttctcc ctggacttgg aagcagatgg acaaccccctc acaccagatg agtacctgac   180
atactccctg aagctgaaga aaggtaccag tcaaaaagat gaaactttta acctgcccag   240
actctgtatc cggaaattct cccaaagaa aaaatgcttt gtctttgatc ggcccgttca   300
ccgcaggaag cttgcccagc tcgagaaact acaagatgaa gagctggacc ccgaatttgt   360
gcaacaagta gcagacttct gttcctacat ctttagtaat tccaaaacta aaactctttc   420
aggaggcatc caggtcaacg ggcctc                                        446
```

<210> SEQ ID NO 3
<211> LENGTH: 494
<212> TYPE: DNA
<213> ORGANISM: Homo sapiens
<220> FEATURE:
<221> NAME/KEY: prim_transcript
<222> LOCATION: (1)..(494)

<400> SEQUENCE: 3

```
gtctagagag cctggtgctg acctacgtca atgccatcag cagtggggat ctaccctgca    60
tggagaacgc agtcctggcc ttggcccaga tagagaactc agccgcagtg gaaaaggcta   120
```

| | |
|---|---|
| ttgcccacta tgaacagcag atgggccaga aggtgcagct gcccacggaa accctccagg | 180 |
| agctgctgga cctgcacagg gacagtgaga gagaggccat tgaagtcttc atgaagaact | 240 |
| ctttcaagga tgtggaccaa atgttccaga ggaaattagg ggcccagttg aagcaaggc | 300 |
| gagatgactt ttgtaagcag aattccaaag catcatcaga ttgttgcatg gctttacttc | 360 |
| aggatatatt tggcccttta gaagaagatg tcaagcaggg aacatttct aaaccaggag | 420 |
| gttaccgtct ctttactcag aagctgcagg agctgaagaa taagtactac caggtgccaa | 480 |
| ggaagggat acag | 494 |

<210> SEQ ID NO 4
<211> LENGTH: 1783
<212> TYPE: DNA
<213> ORGANISM: Homo sapiens
<220> FEATURE:
<221> NAME/KEY: prim_transcript
<222> LOCATION: (1)..(1783)

<400> SEQUENCE: 4

| | |
|---|---|
| aggcacaagt gaaagcagaa gctgaaaagg ctgaagcgca aaggttggcg gcgattcaaa | 60 |
| ggcagaacga gcaaatgatg caggagaggg agagactcca tcaggaacaa gtgagacaaa | 120 |
| tggagatagc caaacaaaat tggctggcag agcaacagaa aatgcaggaa caacagatgc | 180 |
| aggaacaggc tgcacagctc agcacaacat tccaagctca aaatagaagc cttctcagtg | 240 |
| agctccagca cgcccagagg actgttaata cgatgatcc atgtgtttta ctctaaagtg | 300 |
| ctaaatatgg gagtttcctt tttttactct ttgtcactga tgacacaaca gaaagaaac | 360 |
| tgtagacctt gggacaatca acatttaaat aaactttata attattttt caaactttca | 420 |
| tatagagtta taagattatg atgctggtat ctggtaaaat gtacatccca gtagtccaat | 480 |
| agtttaaatg tttattgctt cctttaagag attataaatt gtataaggga cattgtatca | 540 |
| ctgccttcat ttatgcgtga tattgggatg gtttcatcag gagatgcttt ccttgcatct | 600 |
| caatgtcatc tgtctaattt ctcataaggg gattatgtta cctagagcag ggcttcccaa | 660 |
| ccctcaggcc atagactagc tctgatctgt ggcctcttag gaacccggcc acacagcagg | 720 |
| aggtgagcag caggtaagtg agcattacag cctgagctcc acctcctgtc agatcagcag | 780 |
| tgacattaga ttctcacagg agtgggaacc ctattgtgaa ctgtgcatgc aaaagatcta | 840 |
| ggttgtgtga tccttgtgga acaatataaa ccagaaacca ataacgccac cccacctcca | 900 |
| accccgcca accctctgtg gaaaaattac cttccacgaa actggtccct gatgccaaat | 960 |
| aggttgggg accgctgacc tagagggagt tatgcacatg ggcttataag gttagccaag | 1020 |
| agaaaggaca agaagaccca agtcggcaa gcaaatttat taacctgctg ggctgctcta | 1080 |
| cagaaatctg aggaggcaga caccgggctt acaggctaag gggtataagt aggtctgcag | 1140 |
| gggttttgtg tgtgtgtgcg ggggtgtcgg ggggcaagg ccatttgtgg agacttttcc | 1200 |
| tcccagtatg gccacatcct gcagtttgtc agttttgcc cccgcctggc tcagggtacc | 1260 |
| aggatgtggt ttagcttagg ggtggttata gtggcaccta agttctggga acttgcggtg | 1320 |
| ggggcgacct tttggacgaa aaataagctg cagggcagct aggggagggg gcttgttata | 1380 |
| ttcctctggg ggcagggtgt ccctaactgg gctcagtcgg aaggaacttg accaaagtct | 1440 |
| gggctcagtt gggcatcact caggctaatg gtcgtgtgct ggatgccatc agagggaagt | 1500 |
| accaatggta aagtggaaac aatgtgcagc tttcaactgg gtggaggctg ctattctgtg | 1560 |
| gacagtgaga tgtttccttg gcactgtcaa tagacaatct gcgtagagaa attccaagct | 1620 |

```
gaaagccaat aatgttataa taaaatagag attcttcaga agatgaaagg aattaccagc    1680
atggaaattg tgtcataggc ttaagggcta aagaagaagc cttttctttt ctgttcaccc    1740
tcaccaagag cacaacttaa atagggcatt ttataacctg aac                      1783
```

BIOMARKERS FOR PROSPECTIVE DETERMINATION OF RISK FOR DEVELOPMENT OF ACTIVE TUBERCULOSIS

FIELD OF THE INVENTION

This invention relates to a prognostic method for determining the risk of an asymptomatic human subject with latent tuberculosis (TB) infection or apparent latent TB infection and/or after suspected exposure to TB progressing to active tuberculosis disease comprising the steps of quantifying and computationally analysing relative abundances of a collection of pairs of gene products ("TB biomarkers") derived from a sample obtained from the subject. The invention further relates to a collection of TB biomarkers that generates a transcriptomic signature of risk for prediction of the likelihood of an asymptomatic human subject with latent TB infection and/or after suspected exposure to TB progressing to active tuberculosis disease. Furthermore, a kit comprising gene-specific primers or oligonucleotide probes for the detection of pairs of TB biomarkers that generates a prognostic signature of risk for use with the method of the invention is described. In addition, the invention relates to a method of preventive treatment or prophylaxis for TB infection comprising the use of the prognostic method and/or the kit of the invention to select an appropriate or experimental treatment regime or intervention for the human subject and/or to monitor the response of the human subject to the TB prophylaxis.

BACKGROUND OF THE INVENTION

*Mycobacterium tuberculosis* and other mycobacteria cause tuberculosis (TB). One third of the global population is latently infected with *Mycobacterium tuberculosis*, but only 5-10% will progress to active tuberculosis disease during their life-time, while the majority will remain healthy with latent *Mycobacterium tuberculosis* infection. Risk of progression from latent to active tuberculosis is associated with young or old age, co-morbidities such as HIV infection and diabetes mellitus, socioeconomic and nutritional compromise, and therapy with immune modulatory agents such as tumour necrosis factor inhibitors, among others. The current vaccines to prevent TB disease are not sufficiently efficacious, while diagnosis and methods to treat patients with active tuberculosis disease are not having an acceptable impact on the TB epidemic. According to the World Health Organization (WHO), 1.5 million people died of tuberculosis in 2013 (WHO 2014), mediacentre factsheet).

Until now, it has not been possible to predict which individuals with latent asymptomatic tuberculosis (i.e. before the onset of TB symptoms) will develop active tuberculosis, given current tools. The predictive ability of a prognostic method for determining which individuals with latent tuberculosis infection are most at risk of developing active tuberculosis would solve two current problems in preventing deaths from tuberculosis world-wide: (1) the need to accelerate the discovery of effective tuberculosis vaccines and (2) the need to treat those with latent tuberculosis to prevent them from ever developing active tuberculosis. The first solution would allow a determination of which human subjects with latent tuberculosis are most likely to develop active tuberculosis in order to more efficiently, efficaciously, and inexpensively recruit potential human subjects for clinical trials testing prospective tuberculosis vaccines and therapeutics. The second solution would allow identification of those individuals with asymptomatic latent tuberculosis who are likely to develop active tuberculosis disease in order to treat them prophylactically. Importantly, this solution would also spare individuals with asymptomatic latent tuberculosis, who are not at risk of developing active tuberculosis disease, from unnecessarily taking prophylactic TB treatment for many months.

Existing systems biology analyses of disease cohorts have identified diagnostic signatures that discriminate persons with active tuberculosis disease from latent tuberculosis infection and from other disease states (Berry, Graham et al. 2010, Maertzdorf, Ota et al. 2011, Maertzdorf, Repsilber et al. 2011, Bloom, Graham et al. 2012, Maertzdorf, Weiner et al. 2012, Ottenhoff, Dass et al. 2012, Bloom, Graham et al. 2013, Kaforou, Wright et al. 2013, Anderson, Kaforou et al. 2014, Sutherland, Loxton et al. 2014). Such diagnostic signatures would allow testing of ill persons with TB symptoms to determine if they have TB or another respiratory disease with similar clinical presentation as TB. No approach has successfully identified or validated prospective transcriptomic signatures of risk in order to determine whether an asymptomatic subject is likely to progress to active tuberculosis disease (a "Progressor") or not (a "Non-Progressor" or "Control").

Identification of such prognostic transcriptomic signatures of risk for progression to clinical tuberculosis disease prior to manifestation of active disease signs or symptoms would provide a unique opportunity to impact the burden of disease, for example through the implementation of early treatment regimens or targeted enrolment into novel intervention studies.

SUMMARY OF THE INVENTION

According to a first aspect of the invention there is provided a prognostic method for determining the risk of a human subject with asymptomatic tuberculosis (TB) infection or suspected TB infection progressing to active tuberculosis disease, comprising the steps of:

(a) providing a sample from a human subject with asymptomatic TB infection or suspected TB infection;

(b) quantifying and computationally analysing relative abundances of a collection of pairs of gene products ("TB biomarkers"), selected from either:

A. a 6 gene signature consisting of:
  i. 6 PCR-amplified gene products as set out in Table 6 amplified by the oligonucleotide sets as set out in Table 7, forming 9 pairs representing products of the following 6 genes: GBP2; FCGR1 B; SERPING1; TUBGCP6; TRMT2A; SDR39U1 (PCR 6-gene model); or B. a 16 gene signature consisting of any one or both of:
  i. 48 PCR-amplified gene products as set out in Table 3 amplified by the oligonucleotide sets as set out in Table 4 and Table 5, forming 247 pairs, representing products of the following 16 genes: FCGR1C; FCGR1A; STAT1; GBP2; GBP1; GBP4; GBP5; SERPING1; ETV7; BATF2; SCARF1; APOL1; TAP1; TRAFD1; ANKRD22; SEPT4 (PCR PSVM.1 model); and
  ii. 63 mRNA splice junctions as set out in Table 1, forming 258 pairs as set out in Table 2, representing products of the following 16 genes: FCGR1C; FCGR1A; STAT1; GBP2; GBP1; GBP4; GBP5; SERPING1; ETV7; BATF2; SCARF1; APOL1; TAP1; TRAFD1; ANKRD22; and SEPT4 (Junction PSVM.1 model); and (c) computing a prognostic score of the risk of the subject developing active TB disease, thus classifying the subject as "progressor" or "control", wherein a prognostic score of "progressor" indicates that the subject with asymptomatic TB infection or suspected TB infection is likely to progress to active tuberculosis disease.

The asymptomatic tuberculosis infection or suspected TB infection may be latent TB infection in the subject, apparent latent TB infection in the subject, suspected active TB disease in the subject, or after exposure of the subject to TB. For example, the TB infection may be *Mycobacterium tuberculosis* (Mtb), *Mycobacterium bovis* and/or *Mycobacterium africanum* infection.

The computational analysis may comprise the use of one or more coefficients that have been identified by analysis of a prospective TB risk cohort.

In particular, the analysis of the prospective TB risk cohort may take into account the time prior to tuberculosis diagnosis at which each sample of biological materials was obtained from the subjects in the prospective TB risk cohort.

The "progressor" or "control" score may be determined using a reference gene-based mathematical approach whereby:

Score="progressor" if: $a*N1+b*N2+c>0$

Score="control" if: $a*N1+b*N2+c \leq 0$, wherein N1 and N2 represent normalised abundances of two gene products in the pair and coefficients "a", "b" and "c" are those set out in either of Tables 2 or 4 as identified by analysis of a prospective TB risk cohort.

Alternatively or in addition, the "progressor" or "control" score may be determined using a pair ratio-based mathematical approach whereby:

Score="progressor" if: $R1-R2+d>0$

Score="control" if: $R1-R2+d \leq 0$, wherein R1 and R2 represent log-transformed raw abundances of two gene products in the pair and coefficient "d" is as set out in Table 7 as identified by analysis of a TB risk cohort.

For example, the step of quantifying the relative abundances may comprise quantifying expression levels from (i) a splice junction expression dataset or (ii) an amplified gene product dataset.

The computational analysis may comprise the steps of:
(i) quantifying the relative abundances of the 9 pairs of PCR-amplified gene products listed in Table 6 and amplified by the oligonucleotide sets listed in Table 7;
(ii) mathematically associating a coefficient with each of the quantified relative abundances of step (i) to compute a numerical "progressor" or "control" score;
(iii) tallying the "progressor" or "control" scores from all of the pairs of gene products to obtain an overall percentage vote for "progressor" or "control"; and
(iv) predicting the risk of progression to TB disease based on the overall "progressor" or "control" vote obtained from step (iii) above, wherein an overall vote of "progressor" indicates a risk of progression to TB disease in the subject.

In particular, the coefficient may be the coefficient listed in Table 7, matched to the pairs of gene products.

Alternatively or in addition, the step of computational analysis may comprise the steps of:

(i) quantifying the relative abundances of the 247 pairs of PCR-amplified gene products listed in Table 3 and amplified by the oligonucleotide sets listed in Table 4 and 5;
(ii) mathematically associating a coefficient with each of the quantified relative abundances of step (i) to compute a numerical "progressor" or "control" score;
(iii) tallying the "progressor" or "control" scores from all of the pairs of gene products to obtain an overall percentage vote for "progressor" or "control"; and
(iv) predicting the risk of progression to TB disease based on the overall "progressor" or "control" vote obtained from step (iii) above, wherein an overall vote of "progressor" indicates a risk of progression to TB disease in the subject.

In particular, the coefficient may be the coefficient listed in Table 4, matched to the pairs of gene products.

Alternatively or in addition, the step of computational analysis may comprise the steps of:
(i) quantifying the relative abundances of the 258 pairs of splice junctions selected from those listed in Table 2;
(ii) mathematically associating a coefficient with each of the quantified relative abundances of step (i) to compute a numerical "progressor" or "control" score;
(iii) tallying the "progressor" or "control" scores from all of the pairs of gene products to obtain an overall percentage vote for "progressor" or "control"; and
(iv) predicting the risk of progression to TB disease based on the overall "progressor" or "control" vote obtained from step (iii) above, wherein an overall vote of "progressor" indicates a risk of progression to TB disease in the subject.

In particular, the coefficient may be as set out in Table 2, matched to the specific pairs of splice junctions.

The method may further comprise the use of a collection of reference splice junctions listed in Table 8, or reference PCR-amplified gene products amplified by the oligonucleotide sets listed in Table 9 for computing a sample-specific normalisation factor for normalising the relative abundances quantified prior to mathematically associating the quantified abundances in the method.

The relative abundances may be quantified by techniques such as dot blot, quantitative reverse-transcriptase polymerase chain reaction (qRT-PCR), or RNA-Sequencing of RNA extracted from a whole blood sample obtained from the subject, or by any equivalent method for RNA quantification known to those skilled in the art.

The dot blot procedure used may be a cDNA or RNA dot blot procedure. Preferably, the procedure is a miniaturised dot blot such as a microarray.

Many commercial methods for performing RNA-Sequencing, qRT-PCR, hybridization, digital PCR, nanostring technology, reverse transcriptase multiplex ligation-dependent probe amplification (RT-MLPA) and microarray are available and known to those skilled in the art.

The sample may be a biological material.

The biological material may be selected from any one or more of a blood sample, a blood RNA sample, a blood RNA sample derived from whole blood, a blood RNA sample derived from peripheral blood mononuclear cells (PBMCs), a blood RNA sample derived from sorted leukocyte populations, a blood protein sample, a sputum sample, a sputum protein sample, a sputum RNA sample, a tissue RNA sample, or any other RNA sample derived from a human.

The subject may be identified as being likely to progress to active TB disease within 2 years or greater than 2 years from diagnosis with the method of the invention.

The subject may have been treated for TB disease.

According to a further embodiment of the invention there is provided a plurality of primer pairs or oligonucleotide probes as listed in either Table 4, Table 5 or Table 7 for amplification of the PCR-amplified gene products listed in Table 3 or Table 6 respectively for use in a method for determining the risk of a human subject with asymptomatic TB infection or suspected TB infection progressing to active tuberculosis disease.

According to a further embodiment of the invention there is provided a plurality of primer pairs or oligonucleotide probes specific for amplification of and/or binding to each of the splice junctions listed in Table 2 for use in a method for determining the risk of a human subject with asymptomatic TB infection or suspected TB infection progressing to active tuberculosis disease.

According to a further embodiment of the invention there is provided a kit comprising the primer pairs or oligonucleotide probes according to the invention.

The kit may further comprise reference primers or oligonucleotide probes specific for a collection of gene products selected from the group consisting of (i) the reference splice junctions listed in Table 8, or (ii) the reference PCR-amplified gene products amplified by the oligonucleotide sets listed in Table 9 for computing a sample-specific normalisation factor for normalising the relative abundances quantified prior to mathematically associating the quantified abundances in the method.

The kit may additionally comprise instructions for performing the method of the invention.

In particular, the kit may comprise computer readable instructions for each of the steps of quantifying, mathematically associating, tallying, predicting and normalising. In particular, such steps may be performed by one or more computer models or algorithms.

According to a further aspect of the invention, there is provided a method of treatment of a subject comprising the steps of (i) determining the risk of a human subject with asymptomatic TB infection or suspected TB infection progressing to active tuberculosis disease with the use of the method or the use of the primers or oligonucleotide probes or the kit of the invention, followed by (ii) prophylactic TB treatment of the subject when the subject is identified as having a risk of progression to active tuberculosis disease. The method may comprise a further step of determining the risk of the human subject to progress to active tuberculosis following the prophylactic treatment. The method may further comprise a step of on-going monitoring of human subjects identified as not having a risk of progression to active tuberculosis disease with the prognostic method or the use of the primers or oligonucleotide probes or the kit of the invention.

According to a further aspect of the invention, there is provided a method of monitoring a subject for successful prophylactic or therapeutic treatment against TB infection, or risk of recurrence of TB disease after treatment, comprising determining the risk of progression to active tuberculosis disease in the subject with the method or the use of the primers or oligonucleotide probes or the kit of the invention prior to the subject undergoing prophylactic or therapeutic treatment for TB, followed by repeating the method of the invention subsequent to the subject having undergone prophylactic or therapeutic treatment for tuberculosis, wherein a decrease in the risk of progression after treatment compared to prior to treatment is indicative of the efficacy of the prophylactic or therapeutic treatment.

According to a further aspect of the invention, there is provided a method of reducing the incidence of active TB or preventing active TB in a subject comprising the steps of (i) determining the risk of a human subject with asymptomatic TB infection or suspected TB infection progressing to active tuberculosis disease with the use of the method or the use of the primers or oligonucleotide probes or the kit of the invention, followed by (ii) prophylactic TB treatment of the subject when the subject is identified as having a risk of progression to active tuberculosis disease. The method may further comprise a step of on-going monitoring of human subjects identified as not having a risk of progression to active tuberculosis disease with the prognostic method or the use of the primers or oligonucleotide probes or the kit of the invention.

According to a further aspect of the invention, there is provided a method of reducing the mortality rate due to active TB comprising the steps of (i) determining the risk of a human subject with asymptomatic TB infection or suspected TB infection progressing to active tuberculosis disease with the use of the method or the use of the primers or oligonucleotide probes or the kit of the invention, followed by (ii) prophylactic TB treatment of the subject when the subject is identified as having a risk of progression to active tuberculosis disease. The method may further comprise a step of on-going monitoring of human subjects identified as not having a risk of progression to active tuberculosis disease with the prognostic method or the use of the primers or oligonucleotide probes or the kit of the invention.

Such a TB treatment may include any one or more of: isoniazid, rifampicin, rifapentine, ethambutol, pyrazinamide, or any other approved or novel prophylactic or therapeutic TB treatment, vaccine or intervention regimen for a subject.

The method may further comprise performing one or more additional tests for progression of TB infection known to those skilled in the art including QuantiFERON® TB Gold In-Tube test, QuantiFERON® TB Gold Plus test, tuberculin skin test, TB GeneXpert, Xpert MTB/RIF® or other PCR tests, sputum smear microscopy, urine metabolite test, chest x-ray and the like on the subject.

DETAILED DESCRIPTION OF THE INVENTION

Figure 1:
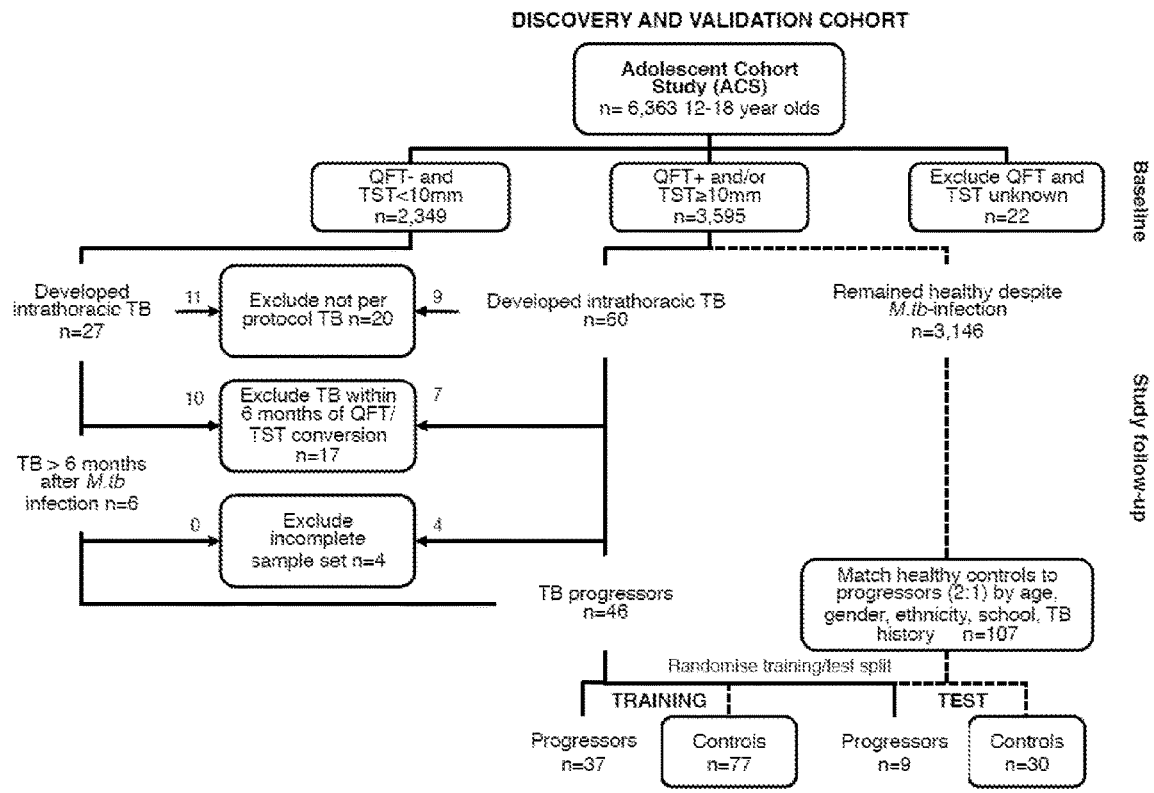
FIG. 1 shows the Adolescent Cohort Study (ACS) and the Grand Challenges 6-74 Study (GC6-74) cohorts for the discovery and validation of signatures of risk for tuberculosis disease. (A) Inclusion and exclusion of participants from the ACS and assignment of eligible progressors and controls to the training and test sets. QFT: QuantiFERON® Gold In-Tube. TST: tuberculin skin test. (B) Inclusion and exclusion of adult household contacts of patients with lung tuberculosis from the GC6-74 cohort, and assignment of eligible progressors and controls to this validation cohort.
Figure 1:
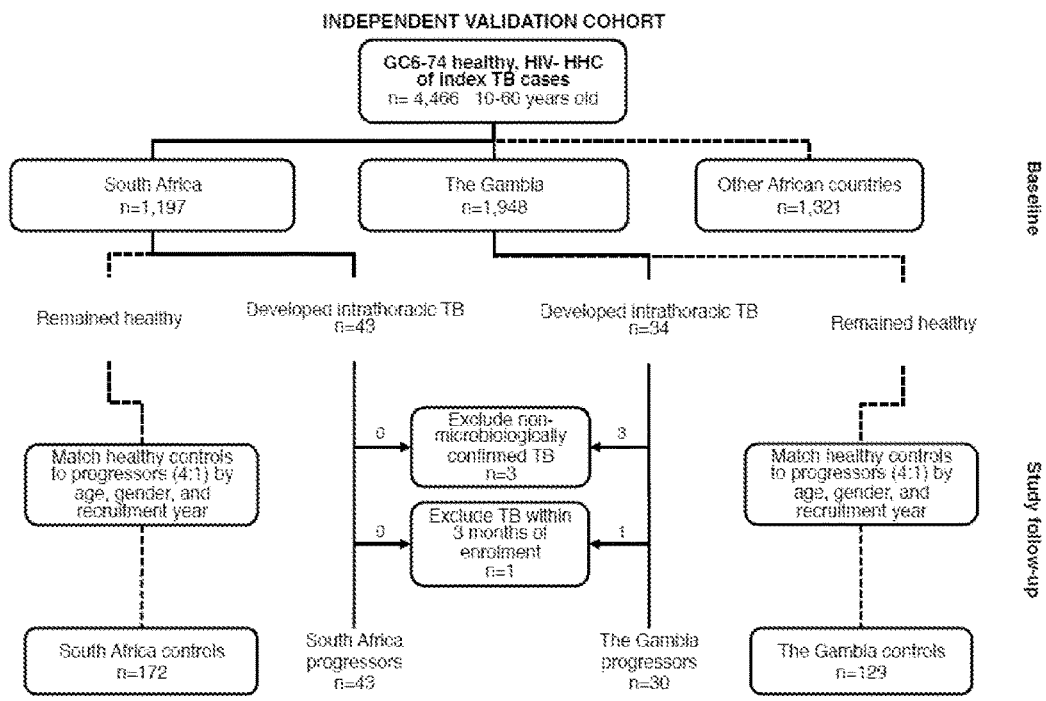

This invention relates to a method of determining the risk of a human subject with asymptomatic tuberculosis (TB) infection, which may be latent TB infection or apparent latent TB infection and/or after suspected exposure to TB progressing to active tuberculosis disease comprising the steps of quantifying and computationally analysing relative abundances of a collection of pairs of gene products ("TB biomarkers") derived from a sample obtained from the subject. The invention was developed through a systems biology analysis of the only suitably designed clinical cohorts to date. In the approach, mathematical algorithms were used based upon the analysis of the temporal progression during which human subjects with asymptomatic tuberculosis were ultimately diagnosed with active tuberculosis, as well as the abundances of gene products revealed during that timescale, in order to computationally determine several TB Biomarkers. The identified signatures predict development of tuberculosis disease across a variety of ages (adolescents and adults), infection and exposure statuses, and ethnicities and geographies.

The present invention provides the first validated prognostic method to determine which individuals with an asymptomatic tuberculosis infection should or should not be diagnostically screened for signs and symptoms for diagnosis of active TB disease, or who should or should not be given prophylactic chemotherapy to prevent the onset of active TB disease, and to prevent the spread of TB infection to other individuals.

In particular, the term "gene products" refers to gene messenger RNAs or fragments of gene messenger RNA fragments, splice junction sites within gene messenger RNAs, or PCR amplicons after PCR amplification of complementary DNA derived from gene messenger RNAs. For example, PCR amplification may be performed by TaqMan primers or others known to those skilled in the art.

As used herein, the term "gene" refers to a unit of inheritance, including the protein coding and noncoding transcribed regions, upstream and downstream regulatory regions, transcribed regions, and all variants of the mature transcript, including microRNAs.

As used herein the term "transcriptome" means the sum total of all the messenger RNA (mRNA) molecules expressed from the genes of an organism.

As used herein, the terms "RNA" and "RNA transcript" are used interchangeably and mean an RNA molecule transcribed from the DNA of a gene.

As used herein, the term "progressor" means an asymptomatic, otherwise healthy individual who does not have definite or suspected TB disease, despite other possible infections or diseases, who developed definite TB disease during follow-up in either the ACS or GC6 studies.

As used herein, "prognostic" means an indication of infection in an otherwise healthy individual before the onset of the TB disease symptoms which would typically trigger health seeking behavior and subsequent diagnosis.

As used herein, the phrase "splice junction" means the nucleic acid sequence in a mature mRNA that results from the joining of two exons encoded by the same gene. "Pairs of mRNA splice junctions" means a set of discrete splice junctions encoded by different genes.

As used herein, the phrase "pair-wise support-vector machine ensemble models" or "PSVM" means collections of multiple simple linear discriminant models, each comprising a pair of mRNA splice junctions encoded by different genes, parameterized using support vector machines (SVM), where the final prediction is the average vote from the whole model collection.

As used herein, the term "oligonucleotide" means a short single-stranded nucleic-acid chain (either as an oligodeoxynucleotide or oligoribonucleotide).

As used herein, the term "active tuberculosis disease" means a diagnosis of tuberculosis disease based on a positive microbiology laboratory test using sputum or another respiratory specimen that confirms detection of acid-fast bacilli, including XpertTB-RIF®, smear microscopy or sputum culture test.

As used herein, the term "coefficient" means a value determined by analysis of a reference set of progressor and control samples, using the support vector machine algorithm, linear discriminant analysis, direct search, or any other suitable methodology.

The molecular techniques referenced herein, including RNA extraction and purification, RNA sequencing, amplification, primer and oligonucleotide probe design, microarray printing and methods, and qRT-PCR are all standard methods known to those skilled in the art. Many reference sources are available, including but not limited to: *Qiagen Molecular Biology Methods*, Methods in Molecular Biology, Ed. J. M. Walker, HumanaPress, ISSN: 1064-3745, Molecular Cloning: A Laboratory Manual by Michael R Green and Joseph Sambrook 2012, Cold Spring Harbour Laboratory Press, ISBN: 978-1-936113-42-2, Molecular cloning: a laboratory manual by Tom Maniatis, E. F. Fritsch, Joseph Sambrook 1982, Cold Spring Harbour Laboratory Press and others known to those skilled in the art.

Mathematically, the TB biomarkers may take one of two forms which differ in terms of the manner in which relative abundances of gene products are analysed to obtain "progressor" or "control" scores:

(1) Reference gene-based: In this approach, the measured relative abundance of a given gene product is normalised by log-transforming and then subtracting the average log-transformed abundance of a set of $N_R$ reference gene products R. For gene products that are not naturally in log space (for example, mRNA abundance measured by RNA-sequencing), the normalised value 'n' of the raw counts of any variable 'v' for a given sample is computed as $$n = \log_2(v+1) - \frac{1}{N_R}\sum_{r \in R} \log_2(r+1).$$

For datasets that are naturally in log space (for example, the cycle thresholds (Cts) of qRT-PCR), the normalised value 'n' of the raw value of any variable 'v' for a given sample is computed as $$n = v - \frac{1}{N_R}\sum_{r \in R} r.$$

The "progressor" or "control" score for the pair of gene products is determined mathematically by:

Score="progressor" if: $a*N1+b*N2+c>0$

Score="control" if: $a*N1+b*N2+c\leq 0$.

where N1 and N2 represent the normalised abundances of the two gene products in the pair. The coefficients "a", "b" and "c" are determined by analysis of a reference set of progressor and control samples, using the support vector machine algorithm, linear discriminant analysis, direct search, or any other suitable methodology. The coefficients in Tables 2, 4 and 6 were computed using the linear SVM algorithm 'Sequential Minimal Optimization', as described in Platt (1998) (Platt 1998).

The mathematical framework for the signatures is a generalization of the k-top-scoring pairs (k-TSP) methodology, which was developed for discovery of cancer biomarkers from microarray datasets (Shi, Ray et al. 2011). Signatures derived using the k-TSP approach are collections of gene product-pair discriminators that can vote "progressor" (1) or "control" (0) (for example). For a given sample, the classification "score" is the average of all of the "0" or "1" votes computed for the whole collection of discriminators for that sample. In this manner, k-TSP combines many "weak" discriminators to improve the reliability of the predictions. The pair-wise discriminators underlying k-TSP are very simple, involving only a pair of gene products for which gene product 1>gene product 2 in progressors and the reverse is true in controls (for example).

Use of the k-TSP framework was desirable to the applicants for three reasons. First, it has the potential to identify combinations of gene products that better predict progression than either gene product individually, a characteristic common to bivariate approaches (Wang, Gerstein et al. 2009). Second, being based on an ensemble of models, rather than a single model, the methodology is tolerant to failed measurements. For example, if a particular primer fails for a particular sample, the overall score can still be computed from the unaffected pairs. In this regard, k-TSP is similar to Random Forests (Owzar, Barry et al. 2011). Third, the underlying models, involving only two gene products, are parsimonious and are therefore unlikely to suffer from overfitting. (Platt 1998)

The applicants replaced the simple rank-based gene product pair models in k-TSP with linear SVM gene pair discriminant models, and call the approach "PSVM" (pairwise support vector machine ensembles). This generalization allows for greater flexibility in the selection of gene product expression patterns that predict tuberculosis progression. While the k-TSP approach requires the relative ranking of the gene products to change between the two conditions (effectively favouring gene pairs that are differentially expressed in opposite directions) any pair of gene products that provides non-redundant information for predicting tuberculosis can be combined in a linear SVM discriminant. This was important for tuberculosis progression, where gene products with the largest magnitude expression differences between progressors and controls tend to be expressed higher in progressors. By merging the k-TSP approach with SVMs, PSVM is similar to the k-TSP modification proposed by Shi et al., (2011) (Shi, Ray et al. 2011). The difference between the method of Shi et al. (2011) (Shi, Ray et al. 2011) and PSVM is that the former replaces the ensemble-based structure with a single SVM model, while PSVM retains the ensemble structure and replaces the rank-based pairs with SVMs internally.

(2) Pair ratio-based: In this approach, the relative abundances of two gene products are directly compared, without first normalising them by reference gene products. The "progressor" or control score for the pair of junctions is determined mathematically by:

Score="progressor" if: $R1-R2+d>0$

Score="control" if: $R1-R2+d \leq 0$.

Where R1 and R2 represent the log-transformed raw abundances of the two gene products in the pair. The coefficient "d" is determined by analysis of a reference set of progressor and control samples by direct search. The difference R1-R2 is computed for all samples in the reference set, and these differences are ranked. A trial set of parameters S is constructed consisting of the midpoint between each successive (R1-R2) difference. For each possible value "s" in S, the sensitivity and specificity are computed on the reference set of samples. "d" is then chosen to be the parameter "s" that maximizes sensitivity+specificity.

As described above, the individual gene product pair models vote "progressor" or "control", and the percentage of pairs within the collection that vote "progressor" provides a score that can be used to assign a sample to the class "progressor" or "control."

Whether a particular score corresponds to a "progressor" or "control" prediction depends on the "vote threshold", which can be dialed to tune the sensitivity/specificity. For higher sensitivity at the cost of lower specificity, a vote threshold <50% can be used; for higher specificity at the cost of lower sensitivity, a vote threshold >50% can be used. In this manner, varying the vote threshold to declare a sample as "progressor" may be adjusted to balance sensitivity and specificity as necessary to meet performance objectives and to account for known parameters in a population, such as application within individuals with known HIV-infection.

In particular, the coefficients may be selected from the coefficients listed in Table 2, matched to the specific pairs of splice-junctions or those listed in Tables 4 or 7, matched to the specific pairs of oligonucleotide sets.

For example, the coefficients listed in Tables 4 and 7 may be influenced by the PCR cycle threshold (Ct), or number of real-time PCR cycles required to record fluorescent signal above the positivity threshold indicating detection of nucleic acid amplification above background, and the identity of the pairs of TaqMan primers for use.

Tables 1 to 9 set out examples of junction pairs and PCR primer pairs used in the computational analysis models of the invention, including coefficients for computation of a numerical "progressor" or "control" scores.

Table 10 sets out the performance statistics of the junction- and PCR primer models used.

TABLE 1

63 unique gene product splice junctions
used in Junction PSVM.1 model

| Unique Junctions | Gene |
|---|---|
| chr1: 120935468-120935863.- | FCGR1B |
| chr2: 191872387-191873688.- | STAT1 |
| chr1: 89578367-89579698.- | GBP2 |
| chr1: 89523917-89524523.- | GBP1 |
| chr11: 57367850-57369507.+ | SERPING1 |
| chr1: 120930293-120934380.- | FCGR1B |
| chr6: 36334539-36334651.- | ETV7 |
| chr11: 64762021-64764347.- | BATF2 |
| chr2: 191845395-191847108.- | STAT1 |
| chr1: 89575949-89578142.- | GBP2 |
| chr17: 1540149-1540234.- | SCARF1 |
| chr2: 191849119-191850344.- | STAT1 |

TABLE 1-continued 63 unique gene product splice junctions used in Junction PSVM.1 model

| Unique Junctions | Gene |
|---|---|
| chr22: 36657768-36661196.+ | APOL1 |
| chr6: 36322464-36334651.- | ETV7 |
| chr1: 89728468-89729418.- | GBP5 |
| chr1: 89524726-89524999.- | GBP1 |
| chr11: 57365794-57367351.+ | SERPING1 |
| chr1: 89520898-89521698.- | GBP1 |
| chr6: 32820016-32820164.- | TAP1 |
| chr2: 191850386-191851579.- | STAT1 |
| chr11: 57369642-57373482.+ | SERPING1 |
| chr17: 1540356-1542099.- | SCARF1 |
| chr2: 191864430-191865799.- | STAT1 |
| chr2: 191851673-191851764.- | STAT1 |
| chr11: 57374020-57379300.+ | SERPING1 |
| chr2: 191847244-191848367.- | STAT1 |
| chr1: 89521911-89522536.- | GBP1 |
| chr1: 149760173-149761609.+ | FCGR1A |
| chr2: 191840613-191841565.- | STAT1 |
| chr12: 112587675-112589604.+ | TRAFD1 |
| chr1: 89519151-89520364.- | GBP1 |
| chr1: 89575553-89575846.- | GBP2 |
| chr1: 89520558-89520795.- | GBP1 |
| chr11: 57374020-57379189.+ | SERPING1 |
| chr1: 89525109-89525879.- | GBP1 |
| chr17: 1542220-1542932.- | SCARF1 |
| chr11: 57373686-57373880.+ | SERPING1 |
| chr2: 191848466-191849035.- | STAT1 |
| chr17: 1543960-1546735.- | SCARF1 |
| chr1: 89579979-89582674.- | GBP2 |
| chr1: 89522817-89523674.- | GBP1 |
| chr17: 56598521-56598614.- | SEPT4 |
| chr2: 191851794-191854340.- | STAT1 |
| chr2: 191856046-191859786.- | STAT1 |
| chr2: 191844592-191845345.- | STAT1 |
| chr11: 57379409-57381800.+ | SERPING1 |
| chr1: 89575949-89578154.- | GBP2 |
| chr1: 89573974-89575359.- | GBP2 |
| chr2: 191854400-191855953.- | STAT1 |
| chr1: 120928615-120930038.- | FCGR1B |
| chr1: 89528936-89530842.- | GBP1 |
| chr1: 89526007-89528727.- | GBP1 |
| chr6: 36336848-36339106.- | ETV7 |
| chr1: 89586953-89587459.- | GBP2 |
| chr2: 191843727-191844497.- | STAT1 |
| chr1: 89654477-89655720.- | GBP4 |
| chr1: 149754330-149754725.+ | FCGR1A |
| chr10: 90588423-90591591.- | ANKRD22 |
| chr17: 1543036-1543205.- | SCARF1 |
| chr1: 89726500-89727902.- | GBP5 |
| chr6: 32818926-32819885.- | TAP1 |
| chr1: 89585971-89586825.- | GBP2 |
| chr2: 191841751-191843581.- | STAT1 |

TABLE 2

Junction PSVM.1 Model of 258 pairs from 63 unique gene product splice junctions representing products of 16 genes using normalised discriminants.

| Junction #1 | Gene #1 | Junction #2 | Gene #2 | Coefficient a | Coefficient b | Coefficient c |
|---|---|---|---|---|---|---|
| chr1: 120935468-120935863.- | FCGR1B | chr1: 89575949-89578154.- | GBP2 | 0.285207 | 2.1199 | 0.376714- |
| chr2: 191872387-191873688.- | STAT1 | chr1: 89575553-89575846.- | GBP2 | 0.350436 | 2.37555 | 0.489671 |
| chr2: 191872387-191873688.- | STAT1 | chr17: 1542220-1542932.- | SCARF1 | 1.25932 | 0.967196 | 4.73381 |
| chr1: 89578367-89579698.- | GBP2 | chr1: 89523917-89524523.- | GBP1 | 1.27049 | 0.930464 | 1.89463 |
| chr1: 89578367-89579698.- | GBP2 | chr2: 191845395-191847108.- | STAT1 | 1.77794 | 1.11019 | 0.200469 |
| chr1: 89578367-89579698.- | GBP2 | chr17: 1540149-1540234.- | SCARF1 | 2.1627 | 0.959494 | 3.13444 |
| chr1: 89578367-89579698.- | GBP2 | chr2: 191849119-191850344.- | STAT1 | 1.367 | 1.35478 | 1.40304 |
| chr1: 89578367-89579698.- | GBP2 | chr11: 57365794-57367351.+ | SERPING1 | 1.2144 | 0.520509 | 2.09552 |
| chr1: 89578367-89579698.- | GBP2 | chr1: 89520898-89521698.- | GBP1 | 1.54259 | 0.580854 | 0.7486 |
| chr1: 89578367-89579698.- | GBP2 | chr6: 32820016-32820164.- | TAP1 | 1.67403 | 1.38444 | 0.0359936 |
| chr1: 89578367-89579698.- | GBP2 | chr2: 191850386-191851579.- | STAT1 | 1.65717 | 1.16995 | 0.737359 |
| chr1: 89578367-89579698.- | GBP2 | chr11: 57369642-57373482.+ | SERPING1 | 1.5283 | 0.438647 | 0.969593 |
| chr1: 89578367-89579698.- | GBP2 | chr2: 191847244-191848367.- | STAT1 | 1.6639 | 1.11452 | 0.28645- |
| chr1: 89578367-89579698.- | GBP2 | chr2: 191840613-191841565.- | STAT1 | 1.45652 | 1.10909 | 0.0326359 |
| chr1: 89578367-89579698.- | GBP2 | chr11: 57374020-57379189.+ | SERPING1 | 1.07994 | 0.658371 | 1.91199 |
| chr1: 89578367-89579698.- | GBP2 | chr17: 1542220-1542932.- | SCARF1 | 2.1514 | 0.971049 | 3.28898 |
| chr1: 89578367-89579698.- | GBP2 | chr11: 57373686-57373880.+ | SERPING1 | 1.39071 | 0.523026 | 1.21026 |
| chr1: 89578367-89579698.- | GBP2 | chr2: 191848466-191849035.- | STAT1 | 1.5105 | 1.43482 | 0.623926 |
| chr1: 89578367-89579698.- | GBP2 | chr2: 191854400-191855953.- | STAT1 | 1.96902 | 0.855648 | 0.502819 |

TABLE 2-continued

Junction PSVM.1 Model of 258 pairs from 63 unique gene product splice junctions representing products of 16 genes using normalised discriminants.

| Junction #1 | Gene #1 | Junction #2 | Gene #2 | Coefficient a | Coefficient b | Coefficient c |
|---|---|---|---|---|---|---|
| chr1: 89523917-89524523.- | GBP1 | chr1: 120930293-120934380.- | FCGR1B | 1.29497 | 0.17888 | 3.35203 |
| chr1: 89523917-89524523.- | GBP1 | chr6: 36334539-36334651.- | ETV7 | 1.02884 | 0.337848 | 4.38101 |
| chr1: 89523917-89524523.- | GBP1 | chr11: 64762021-64764347.- | BATF2 | 1.22054 | 0.238532 | 4.39808 |
| chr1: 89523917-89524523.- | GBP1 | chr1: 89575949-89578142.- | GBP2 | 0.976243 | 1.1819 | 7.7377 |
| chr1: 89523917-89524523.- | GBP1 | chr2: 191849119-191850344.- | STAT1 | 1.05268 | 0.744786- | 3.41572 |
| chr1: 89523917-89524523.- | GBP1 | chr1: 89524726-89524999.- | GBP1 | 2.13879 | 0.716641 | 3.55457 |
| chr1: 89523917-89524523.- | GBP1 | chr11: 57365794-57367351.+ | SERPING1 | 0.754011 | 0.507927 | 4.108 |
| chr1: 89523917-89524523.- | GBP1 | chr1: 89520898-89521698.- | GBP1 | 1.14209 | 0.346987 | 3.29321 |
| chr1: 89523917-89524523.- | GBP1 | chr6: 32820016-32820164.- | TAP1 | 1.09951 | 0.990063 | 2.85177 |
| chr1: 89523917-89524523.- | GBP1 | chr2: 191850386-191851579.- | STAT1 | 1.25538 | 0.416079- | 3.31666 |
| chr1: 89523917-89524523.- | GBP1 | chr2: 191851673-191851764.- | STAT1 | 1.57174 | 0.0901443 | 3.59663 |
| chr1: 89523917-89524523.- | GBP1 | chr2: 191847244-191848367.- | STAT1 | 1.01381 | 0.754036 | 2.74436 |
| chr1: 89523917-89524523.- | GBP1 | chr1: 89521911-89522536.- | GBP1 | 1.07615 | 0.388961 | 3.24632 |
| chr1: 89523917-89524523.- | GBP1 | chr2: 191840613-191841565.- | STAT1 | 1.0067 | 0.813658 | 2.51646 |
| chr1: 89523917-89524523.- | GBP1 | chr12: 112587675-112589604.+ | TRAFD1 | 0.893824 | 1.51204 | 5.57804 |
| chr1: 89523917-89524523.- | GBP1 | chr1: 89519151-89520364.- | GBP1 | 1.20234 | 0.32556 | 3.30171 |
| chr1: 89523917-89524523.- | GBP1 | chr1: 120928615-120930038.- | FCGR1B | 1.27897 | 0.17222 | 3.70181 |
| chr1: 89523917-89524523.- | GBP1 | chr1: 89575553-89575846.- | GBP2 | 0.698719 | 1.82301 | 1.04535 |
| chr1: 89523917-89524523.- | GBP1 | chr1: 89520558-89520795.- | GBP1 | 1.07564 | 0.435851- | 3.20174 |
| chr1: 89523917-89524523.- | GBP1 | chr1: 89525109-89525879.- | GBP1 | 1.71622 | 0.291143 | 3.32571 |
| chr1: 89523917-89524523.- | GBP1 | chr17: 1542220-1542932.- | SCARF1 | 1.1832 | 1.07428 | 6.72211 |
| chr1: 89523917-89524523.- | GBP1 | chr11: 57373686-57373880.+ | SERPING1 | 0.852965 | 0.344637 | 2.97819 |
| chr1: 89523917-89524523.- | GBP1 | chr17: 1543960-1546735.- | SCARF1 | 1.31834 | 0.567278- | 6.32754 |
| chr1: 89523917-89524523.- | GBP1 | chr1: 89528936-89530842.- | GBP1 | 2.36135 | 0.945849 | 3.2198 |
| chr1: 89523917-89524523.- | GBP1 | chr1: 89579979-89582674.- | GBP2 | 0.656619 | 1.92825- | 1.77044 |
| chr1: 89523917-89524523.- | GBP1 | chr1: 89526007-89528727.- | GBP1 | 1.84439 | 0.344796 | 3.48177 |
| chr1: 89523917-89524523.- | GBP1 | chr1: 89522817-89523674.- | GBP1 | 1.34336 | 0.154821 | 3.43695 |
| chr1: 89523917-89524523.- | GBP1 | chr2: 191844592-191845345.- | STAT1 | 1.19401 | 0.47042 | 3.39904 |
| chr1: 89523917-89524523.- | GBP1 | chr11: 57379409-57381800.+ | SERPING1 | 0.91719 | 0.331856 | 3.25813 |
| chr1: 89523917-89524523.- | GBP1 | chr6: 36336848-36339106.- | ETV7 | 1.20774 | 0.348785 | 4.84661 |
| chr1: 89523917-89524523.- | GBP1 | chr1: 89575949-89578154.- | GBP2 | 0.977878 | 1.37234 | 1.9126 |
| chr1: 89523917-89524523.- | GBP1 | chr1: 89573974-89575359.- | GBP2 | 0.849291 | 1.73656 | 1.51782 |
| chr11: 57367850-57369507.+ | SERPING1 | chr1: 89575553-89575846.- | GBP2 | 0.4201 | 1.74942 | 0.759878 |
| chr1: 120930293-120934380.- | FCGR1B | chr1: 89575949-89578142.- | GBP2 | 0.688095 | 1.19105 | 6.68836 |
| chr6: 36334539-36334651.- | ETV7 | chr11: 57365794-57367351.+ | SERPING1 | 0.193764 | 0.788461 | 4.59064 |
| chr6: 36334539-36334651.- | ETV7 | chr1: 89520898-89521698.- | GBP1 | 0.25262 | 1.30924 | 3.81365 |
| chr6: 36334539-36334651.- | ETV7 | chr6: 32820016-32820164.- | TAP1 | 0.356385 | 2.45183 | 2.78492 |

TABLE 2-continued

Junction PSVM.1 Model of 258 pairs from 63 unique gene product splice junctions representing products of 16 genes using normalised discriminants.

| Junction #1 | Gene #1 | Junction #2 | Gene #2 | Coefficient a | Coefficient b | Coefficient c |
|---|---|---|---|---|---|---|
| chr6: 36334539-36334651.- | ETV7 | chr1: 89575553-89575846.- | GBP2 | 0.263486 | 2.37749 | 0.774872 |
| chr6: 36334539-36334651.- | ETV7 | chr1: 89520558-89520795.- | GBP1 | 0.304563 | 1.09326 | 3.4828 |
| chr6: 36334539-36334651.- | ETV7 | chr11: 57374020-57379189.+ | SERPING1 | 0.0418873 | 0.916089 | 3.14604 |
| chr6: 36334539-36334651.- | ETV7 | chr1: 89579979-89582674.- | GBP2 | 0.247109 | 2.24571 | 1.70459 |
| chr6: 36334539-36334651.- | ETV7 | chr2: 191844592-191845345.- | STAT1 | 0.342379 | 1.73174 | 4.0271 |
| chr6: 36334539-36334651.- | ETV7 | chr11: 57379409-57381800.+ | SERPING1 | 0.256834 | 0.785482 | 4.03433 |
| chr6: 36334539-36334651.- | ETV7 | chr1: 89575949-89578154.- | GBP2 | 0.343871 | 2.17762 | 1.40674 |
| chr6: 36334539-36334651.- | ETV7 | chr1: 89573974-89575359.- | GBP2 | 0.308049 | 2.18241 | 1.19864 |
| chr11: 64762021-64764347.- | BATF2 | chr1: 89575949-89578142.- | GBP2 | 0.691134 | 1.54807 | 11.3272 |
| chr11: 64762021-64764347.- | BATF2 | chr11: 57365794-57367351.+ | SERPING1 | 0.083579 | 0.882094 | 4.42096 |
| chr11: 64762021-64764347.- | BATF2 | chr1: 89520898-89521698.- | GBP1 | 0.350794 | 1.00655 | 3.94246 |
| chr11: 64762021-64764347.- | BATF2 | chr1: 89575553-89575846.- | GBP2 | 0.207853 | 2.56211 | 0.409211 |
| chr11: 64762021-64764347.- | BATF2 | chr1: 89520558-89520795.- | GBP1 | 0.3352 | 0.909042 | 3.40701 |
| chr11: 64762021-64764347.- | BATF2 | chr2: 191844592-191845345.- | STAT1 | 0.471162 | 1.4317 | 4.5874 |
| chr11: 64762021-64764347.- | BATF2 | chr11: 57379409-57381800.+ | SERPING1 | 0.230702 | 0.694393 | 3.70174- |
| chr2: 191845395-191847108.- | STAT1 | chr1: 89575553-89575846.- | GBP2 | 0.895636 | 1.792 | 0.316951 |
| chr2: 191845395-191847108.- | STAT1 | chr11: 57374020-57379189.+ | SERPING1 | 0.626705 | 0.714263 | 2.58324 |
| chr2: 191845395-191847108.- | STAT1 | chr17: 1542220-1542932.- | SCARF1 | 1.66295 | 0.78287 | 3.53539- |
| chr2: 191845395-191847108.- | STAT1 | chr1: 89575949-89578154.- | GBP2 | 0.956589 | 1.66393 | 0.0286896- |
| chr2: 191845395-191847108.- | STAT1 | chr1: 89573974-89575359.- | GBP2 | 1.04397 | 1.77107 | 0.0537381 |
| chr1: 89575949-89578142.- | GBP2 | chr1: 89728468-89729418.- | GBP2 | 1.0044 | 0.820216 | 4.8749 |
| chr1: 89575949-89578142.- | GBP2 | chr1: 89520898-89521698.- | GBP1 | 1.10668 | 1.02793 | 6.77529 |
| chr1: 89575949-89578142.- | GBP2 | chr11: 57369642-57373482.+ | SERPING1 | 1.11134 | 0.50891 | 6.50406 |
| chr1: 89575949-89578142.- | GBP2 | chr1: 89519151-89520364.- | GBP1 | 1.23476 | 0.908634 | 6.88704 |
| chr1: 89575949-89578142.- | GBP2 | chr1: 89520558-89520795.- | GBP1 | 0.898153 | 0.937195 | 5.54997 |
| chr1: 89575949-89578142.- | GBP2 | chr11: 57374020-57379189.+ | SERPING1 | 0.973874 | 0.643831 | 6.51772 |
| chr1: 89575949-89578142.- | GBP2 | chr1: 89525109-89525879.- | GBP1 | 1.16956 | 0.883308 | 7.35593 |
| chr1: 89575949-89578142.- | GBP2 | chr11: 57373686-57373880.+ | SERPING1 | 0.998565 | 0.572259 | 6.1963 |
| chr1: 89575949-89578142.- | GBP2 | chr2: 191854400-191855953.- | STAT1 | 1.00109 | 1.37029 | 5.89692 |
| chr1: 89575949-89578142.- | GBP2 | chr2: 191851794-191854340.- | STAT1 | 1.05852 | 1.41084 | 7.24454 |
| chr1: 89575949-89578142.- | GBP2 | chr2: 191844592-191845345.- | STAT1 | 0.990555 | 1.29639 | 6.16574 |
| chr1: 89575949-89578142.- | GBP2 | chr11: 57379409-57381800.+ | SERPING1 | 1.29403 | 0.478362 | 7.47172 |
| chr17: 1540149-1540234.- | SCARF1 | chr11: 57365794-57367351.+ | SERPING1 | 0.896132 | 0.640186 | 6.04489 |
| chr17: 1540149-1540234.- | SCARF1 | chr1: 89520898-89521698.- | GBP1 | 0.965133 | 1.03678 | 5.13361 |
| chr17: 1540149-1540234.- | SCARF1 | chr2: 191840613-191841565.- | STAT1 | 0.992167 | 1.74631 | 3.69583 |
| chr17: 1540149-1540234.- | SCARF1 | chr1: 89519151-89520364.- | GBP1 | 1.0618 | 1.02551 | 5.07092 |
| chr17: 1540149-1540234.- | SCARF1 | chr1: 89575553-89575846.- | GBP2 | 0.590721 | 2.51025 | 1.36676 |

TABLE 2-continued

Junction PSVM.1 Model of 258 pairs from 63 unique gene product splice junctions representing products of 16 genes using normalised discriminants.

| Junction #1 | Gene #1 | Junction #2 | Gene #2 | Coefficient a | Coefficient b | Coefficient c |
|---|---|---|---|---|---|---|
| chr17: 1540149-1540234.- | SCARF1 | chr1: 89586953-89587459.- | GBP2 | 0.67812 | 2.09837 | 2.71962 |
| chr17: 1540149-1540234.- | SCARF1 | chr2: 191851794-191854340.- | STAT1 | 0.947475 | 1.85884 | 6.68639 |
| chr17: 1540149-1540234.- | SCARF1 | chr2: 191844592-191845345.- | STAT1 | 1.23958 | 1.82893 | 6.5906 |
| chr17: 1540149-1540234.- | SCARF1 | chr11: 57379409-57381800.+ | SERPING1 | 1.10524 | 0.670449 | 6.24311 |
| chr17: 1540149-1540234.- | SCARF1 | chr1: 89575949-89578154.- | GBP2 | 0.899751 | 2.0282 | 2.697 |
| chr17: 1540149-1540234.- | SCARF1 | chr1: 89573974-89575359.- | GBP2 | 0.776853 | 2.07753 | 2.12151 |
| chr2: 191849119-191850344.- | STAT1 | chr1: 89575553-89575846.- | GBP2 | 1.05756 | 1.64379 | 0.738719 |
| chr2: 191849119-191850344.- | STAT1 | chr11: 57374020-57379189.+ | SERPING1 | 0.830457 | 0.663751 | 3.20533 |
| chr2: 191849119-191850344.- | STAT1 | chr1: 89579979-89582674.- | GBP2 | 0.927528 | 1.83654 | 1.35414 |
| chr22: 36657768-36661196.+ | APOL1 | chr11: 57365794-57367351.+ | SERPING1 | 0.717374 | 0.611252 | 4.80441 |
| chr6: 36322464-36334651.- | ETV7 | chr2: 191851673-191851764.- | STAT1 | 0.459111 | 1.64107 | 5.2932 |
| chr6: 36322464-36334651.- | ETV7 | chr12: 112587675-112589604.+ | TRAFD1 | 0.398725 | 1.8991 | 7.06468 |
| chr6: 36322464-36334651.- | ETV7 | chr1: 89575553-89575846.- | GBP2 | 0.32217 | 2.01548 | 1.57619 |
| chr6: 36322464-36334651.- | ETV7 | chr11: 57374020-57379189.+ | SERPING1 | 0.314927 | 0.682411 | 4.42219 |
| chr6: 36322464-36334651.- | ETV7 | chr2: 191848466-191849035.- | STAT1 | 0.284887 | 1.86557 | 2.95269 |
| chr6: 36322464-36334651.- | ETV7 | chr2: 191851794-191854340.- | STAT1 | 0.432748 | 1.51699 | 5.76871 |
| chr6: 36322464-36334651.- | ETV7 | chr2: 191843727-191844497.- | STAT1 | 0.409282 | 1.6949 | 4.28407 |
| chr6: 36322464-36334651.- | ETV7 | chr2: 191856046-191859786.- | STAT1 | 0.476751 | 1.35538 | 4.53407 |
| chr6: 36322464-36334651.- | ETV7 | chr2: 191844592-191845345.- | STAT1 | 0.424308 | 1.69962 | 4.98653 |
| chr6: 36322464-36334651.- | ETV7 | chr11: 57379409-57381800.+ | SERPING1 | 0.363947 | 0.67685 | 4.70004 |
| chr6: 36322464-36334651.- | ETV7 | chr1: 89575949-89578154.- | GBP2 | 0.372809 | 1.92462 | 2.08382 |
| chr6: 36322464-36334651.- | ETV7 | chr1: 89573974-89575359.- | GBP2 | 0.363832 | 1.97069 | 1.95929 |
| chr1: 89728468-89729418.- | GBP5 | chr12: 112587675-112589604.+ | TRAFD1 | 0.970286 | 1.43058 | 3.61207 |
| chr1: 89524726-89524999.- | GBP1 | chr12: 112587675-112589604.+ | TRAFD1 | 0.767767 | 1.82419 | 5.69363- |
| chr1: 89524726-89524999.- | GBP1 | chr1: 89575553-89575846.- | GBP2 | 0.201923 | 2.45849 | 0.440964 |
| chr1: 89524726-89524999.- | GBP1 | chr11: 57379409-57381800.+ | SERPING1 | 0.479309 | 0.644786 | 3.21305 |
| chr1: 89524726-89524999.- | GBP1 | chr1: 89575949-89578154.- | GBP2 | 0.416835 | 2.02135 | 0.299378 |
| chr11: 57365794-57367351.+ | SERPING1 | chr1: 89520898-89521698.- | GBP1 | 0.626027 | 0.552874 | 3.77996 |
| chr11: 57365794-57367351.+ | SERPING1 | chr6: 32820016-32820164.- | TAP1 | 0.577921 | 1.16157 | 2.963 |
| chr11: 57365794-57367351.+ | SERPING1 | chr2: 191850386-191851579.- | STAT1 | 0.590859 | 0.967137 | 3.55823 |
| chr11: 57365794-57367351.+ | SERPING1 | chr1: 89521911-89522536.- | GBP1 | 0.631174 | 0.464056 | 3.7025 |
| chr11: 57365794-57367351.+ | SERPING1 | chr2: 191840613-191841565.- | STAT1 | 0.602963 | 0.935745 | 2.84409 |
| chr11: 57365794-57367351.+ | SERPING1 | chr1: 89519151-89520364.- | GBP1 | 0.691435 | 0.422047- | 3.66721 |
| chr11: 57365794-57367351.+ | SERPING1 | chr1: 89654477-89655720.- | GBP4 | 0.973516 | 0.0273947 | 4.26335 |
| chr11: 57365794-57367351.+ | SERPING1 | chr1: 89575553-89575846.- | GBP2 | 0.464062 | 1.45615 | 1.63239 |
| chr11: 57365794-57367351.+ | SERPING1 | chr1: 89520558-89520795.- | GBP1 | 0.681863 | 0.371669 | 3.6218 |
| chr11: 57365794-57367351.+ | SERPING1 | chr1: 89586953-89587459.- | GBP2 | 0.608429 | 1.70932 | 3.03428 |

TABLE 2-continued

Junction PSVM.1 Model of 258 pairs from 63 unique gene product splice junctions representing products of 16 genes using normalised discriminants.

| Junction #1 | Gene #1 | Junction #2 | Gene #2 | Coefficient a | Coefficient b | Coefficient c |
|---|---|---|---|---|---|---|
| chr11: 57365794-57367351.+ | SERPING1 | chr2: 191854400-191855953.- | STAT1 | 0.748584 | 0.505598 | 3.84638 |
| chr11: 57365794-57367351.+ | SERPING1 | chr1: 89579979-89582674.- | GBP2 | 0.433166 | 1.52584- | 2.1781 |
| chr11: 57365794-57367351.+ | SERPING1 | chr1: 89526007-89528727.- | GBP1 | 0.936077 | 0.0385161 | 4.08476 |
| chr11: 57365794-57367351.+ | SERPING1 | chr1: 89522817-89523674.- | GBP1 | 0.77159 | 0.302736 | 4.04944 |
| chr11: 57365794-57367351.+ | SERPING1 | chr1: 149754330-149754725.+ | FCGR1A | 0.885822 | 0.064637 | 4.1202 |
| chr11: 57365794-57367351.+ | SERPING1 | chr2: 191843727-191844497.- | STAT1 | 0.732242 | 0.584394 | 3.82672 |
| chr11: 57365794-57367351.+ | SERPING1 | chr10: 90588423-90591591.- | ANKRD22 | 0.763367 | 0.282725 | 5.07542 |
| chr11: 57365794-57367351.+ | SERPING1 | chr2: 191844592-191845345.- | STAT1 | 0.600896 | 0.914631 | 3.8411 |
| chr11: 57365794-57367351.+ | SERPING1 | chr1: 89575949-89578154.- | GBP2 | 0.526591 | 1.32518 | 1.94513 |
| chr11: 57365794-57367351.+ | SERPING1 | chr1: 89573974-89575359.- | GBP2 | 0.498391 | 1.47598 | 1.82342 |
| chr1: 89520898-89521698.- | GBP1 | chr6: 32820016-32820164.- | TAP1 | 0.997441 | 1.1834 | 2.0519 |
| chr1: 89520898-89521698.- | GBP1 | chr2: 191847244-191848367.- | STAT1 | 0.70947 | 1.1295 | 1.75916 |
| chr1: 89520898-89521698.- | GBP1 | chr12: 112587675-112589604.+ | TRAFD1 | 0.900384 | 1.38342 | 4.78248- |
| chr1: 89520898-89521698.- | GBP1 | chr1: 89575553-89575846.- | GBP2 | 0.429507 | 2.26655 | 0.0290825 |
| chr1: 89520898-89521698.- | GBP1 | chr11: 57373686-57373880.+ | SERPING1 | 0.512866 | 0.535606 | 2.39436 |
| chr1: 89520898-89521698.- | GBP1 | chr1: 89579979-89582674.- | GBP2 | 0.473178 | 2.14672 | 1.03942 |
| chr1: 89520898-89521698.- | GBP1 | chr17: 1543036-1543205.- | SCARF1 | 1.14887 | 0.803721 | 5.29699 |
| chr1: 89520898-89521698.- | GBP1 | chr2: 191844592-191845345.- | STAT1 | 0.865759 | 0.876281 | 2.55002 |
| chr1: 89520898-89521698.- | GBP1 | chr11: 57379409-57381800.+ | SERPING1 | 0.913967 | 0.347821 | 2.75455 |
| chr1: 89520898-89521698.- | GBP1 | chr1: 89575949-89578154.- | GBP2 | 0.481804 | 1.83496 | 0.339283 |
| chr1: 89520898-89521698.- | GBP1 | chr1: 89573974-89575359.- | GBP2 | 0.691559 | 1.80399 | 0.782511 |
| chr6: 32820016-32820164.- | TAP1 | chr1: 89579979-89582674.- | GBP2 | 0.862617 | 2.20617 | 0.509572 |
| chr6: 32820016-32820164.- | TAP1 | chr17: 1543036-1543205.- | SCARF1 | 2.34692 | 0.808373 | 3.86042- |
| chr6: 32820016-32820164.- | TAP1 | chr1: 89575949-89578154.- | GBP2 | 1.45241 | 1.64895 | 0.0960111- |
| chr6: 32820016-32820164.- | TAP1 | chr1: 89573974-89575359.- | GBP2 | 1.43663 | 1.70311 | 0.0180362 |
| chr2: 191850386-191851579.- | STAT1 | chr1: 89575553-89575846.- | GBP2 | 0.821409 | 1.80722 | 0.0372882 |
| chr2: 191850386-191851579.- | STAT1 | chr11: 57374020-57379189.+ | SERPING1 | 0.736367 | 0.641249 | 2.72292 |
| chr2: 191850386-191851579.- | STAT1 | chr17: 1542220-1542932.- | SCARF1 | 1.59312 | 0.950912 | 4.84 |
| chr2: 191850386-191851579.- | STAT1 | chr1: 89579979-89582674.- | GBP2 | 0.850183 | 1.99101 | 1.00519 |
| chr2: 191850386-191851579.- | STAT1 | chr1: 89575949-89578154.- | GBP2 | 0.969629 | 1.53369 | 0.411908 |
| chr2: 191850386-191851579.- | STAT1 | chr1: 89573974-89575359.- | GBP2 | 1.16818 | 1.46204 | 0.556486 |
| chr11: 57369642-57373482.+ | SERPING1 | chr1: 89575553-89575846.- | GBP2 | 0.254478- | 2.26315 | 0.0334622 |
| chr11: 57369642-57373482.+ | SERPING1 | chr11: 57374020-57379189.+ | SERPING1 | 0.0400542 | 1.00536 | 3.08212 |
| chr11: 57369642-57373482.+ | SERPING1 | chr1: 89575949-89578154.- | GBP2 | 0.381369 | 1.52209 | 0.688692 |
| chr11: 57369642-57373482.+ | SERPING1 | chr1: 89573974-89575359.- | GBP2 | 0.446125 | 1.81075 | 0.896503 |
| chr17: 1540356-1542099.- | SCARF1 | chr1: 89575553-89575846.- | GBP2 | 0.442596 | 2.60236 | 0.774971 |
| chr17: 1540356-1542099.- | SCARF1 | chr1: 89579979-89582674.- | GBP2 | 0.297076 | 2.60906 | 1.3743 |

TABLE 2-continued

Junction PSVM.1 Model of 258 pairs from 63 unique gene product splice junctions representing products of 16 genes using normalised discriminants.

| Junction #1 | Gene #1 | Junction #2 | Gene #2 | Coefficient a | Coefficient b | Coefficient c |
|---|---|---|---|---|---|---|
| chr2: 191864430-191865799.- | STAT1 | chr11: 57374020-57379189.+ | SERPING1 | 0.268137 | 0.802996 | 2.85528 |
| chr2: 191864430-191865799.- | STAT1 | chr11: 57379409-57381800.+ | SERPING1 | 0.945158 | 0.557035 | 2.82973 |
| chr2: 191851673-191851764.- | STAT1 | chr12: 112587675-112589604.+ | TRAFD1 | 0.930121 | 1.9892 | 5.7801 |
| chr2: 191851673-191851764.- | STAT1 | chr11: 57379409-57381800.+ | SERPING1 | 0.963846 | 0.552689 | 3.24803 |
| chr11: 57374020-57379300.+ | SERPING1 | chr1: 89575553-89575846.- | GBP2 | 0.220335 | 2.4917 | 0.907318 |
| chr11: 57374020-57379300.+ | SERPING1 | chr1: 89575949-89578154.- | GBP2 | 0.258892 | 2.33237 | 1.40384 |
| chr11: 57374020-57379300.+ | SERPING1 | chr1: 89573974-89575359.- | GBP2 | 0.347316 | 2.23051 | 2.0366- |
| chr2: 191847244-191848367.- | STAT1 | chr1: 89575553-89575846.- | GBP2 | 0.878939 | 1.79169 | 0.177216 |
| chr2: 191847244-191848367.- | STAT1 | chr1: 89575949-89578154.- | GBP2 | 0.995376 | 1.55789 | 0.134965 |
| chr2: 191847244-191848367.- | STAT1 | chr1: 89573974-89575359.- | GBP2 | 1.16465 | 1.7212 | 0.106906 |
| chr1: 89521911-89522536.- | GBP1 | chr1: 89575553-89575846.- | GBP2 | 0.438375 | 1.98003 | 0.108978 |
| chr1: 89521911-89522536.- | GBP1 | chr11: 57374020-57379189.+ | SERPING1 | 0.33544 | 0.691089 | 2.77811- |
| chr1: 149760173-149761609.+ | FCGR1A | chr1: 89575949-89578154.- | GBP2 | 0.000535437 | 2.88083 | 0.705716 |
| chr2: 191840613-191841565.- | STAT1 | chr11: 57374020-57379189.+ | SERPING1 | 0.5192 | 0.736047 | 2.44614 |
| chr2: 191840613-191841565.- | STAT1 | chr17: 1542220-1542932.- | SCARF1 | 1.91004 | 0.800577 | 3.26943 |
| chr2: 191840613-191841565.- | STAT1 | chr11: 57379409-57381800.+ | SERPING1 | 1.2438 | 0.451846 | 1.79781 |
| chr2: 191840613-191841565.- | STAT1 | chr6: 36336848-36339106.- | ETV7 | 1.68502 | 0.441517 | 2.6945- |
| chr2: 191840613-191841565.- | STAT1 | chr1: 89575949-89578154.- | GBP2 | 0.855951 | 1.72107 | 0.302374 |
| chr12: 112587675-112589604.+ | TRAFD1 | chr1: 89520558-89520795.- | GBP1 | 1.46576 | 0.903501 | 4.79357 |
| chr12: 112587675-112589604.+ | TRAFD1 | chr11: 57374020-57379189.+ | SERPING1 | 1.47246 | 0.58668 | 5.22072 |
| chr12: 112587675-112589604.+ | TRAFD1 | chr1: 89525109-89525879.- | GBP1 | 2.09613 | 0.758414 | 6.58906 |
| chr12: 112587675-112589604.+ | TRAFD1 | chr2: 191848466-191849035.- | STAT1 | 1.23714 | 1.34342 | 3.53636 |
| chr12: 112587675-112589604.+ | TRAFD1 | chr1: 89579979-89582674.- | GBP2 | 1.65218 | 1.67172 | 4.0126 |
| chr12: 112587675-112589604.+ | TRAFD1 | chr2: 191844592-191845345.- | STAT1 | 1.62643 | 1.22345 | 5.15275 |
| chr12: 112587675-112589604.+ | TRAFD1 | chr11: 57379409-57381800.+ | SERPING1 | 1.91445 | 0.456435 | 5.96664 |
| chr12: 112587675-112589604.+ | TRAFD1 | chr1: 89575949-89578154.- | GBP2 | 1.30418 | 1.74797 | 2.67285 |
| chr12: 112587675-112589604.+ | TRAFD1 | chr1: 89726500-89727902.- | GBP5 | 1.42336 | 1.04659 | 3.90109- |
| chr1: 89519151-89520364.- | GBP1 | chr1: 89575553-89575846.- | GBP2 | 0.361017 | 2.25221 | 0.282973 |
| chr1: 89519151-89520364.- | GBP1 | chr11: 57374020-57379189.+ | SERPING1 | 0.308618 | 0.726964 | 2.72249 |
| chr1: 89519151-89520364.- | GBP1 | chr1: 89579979-89582674.- | GBP2 | 0.367995 | 2.2807 | 0.718353 |
| chr1: 89519151-89520364.- | GBP1 | chr1: 89575949-89578154.- | GBP2 | 0.715311 | 1.42619 | 0.529364 |
| chr1: 89519151-89520364.- | GBP1 | chr1: 89573974-89575359.- | GBP2 | 0.814194 | 1.43513 | 0.630707- |
| chr1: 89575553-89575846.- | GBP2 | chr1: 89520558-89520795.- | GBP1 | 2.39997 | 0.257961 | 0.445099 |
| chr1: 89575553-89575846.- | GBP2 | chr11: 57374020-57379189.+ | SERPING1 | 1.77085 | 0.426625 | 0.851148- |
| chr1: 89575553-89575846.- | GBP2 | chr6: 32818926-32819885.- | TAP1 | 2.10893 | 0.994396 | 0.602493- |
| chr1: 89575553-89575846.- | GBP2 | chr1: 89525109-89525879.- | GBP1 | 2.37697 | 0.256124 | 0.230497 |
| chr1: 89575553-89575846.- | GBP2 | chr17: 1542220-1542932.- | SCARF1 | 2.41941 | 0.529672 | 1.13848 |

TABLE 2-continued

Junction PSVM.1 Model of 258 pairs from 63 unique gene product splice junctions representing products of 16 genes using normalised discriminants.

| Junction #1 | Gene #1 | Junction #2 | Gene #2 | Coefficient a | Coefficient b | Coefficient c |
|---|---|---|---|---|---|---|
| chr1: 89575553-89575846.- | GBP2 | chr11: 57373686-57373880.+ | SERPING1 | 1.95151 | 0.387175 | 0.494035- |
| chr1: 89575553-89575846.- | GBP2 | chr2: 191848466-191849035.- | STAT1 | 1.68655 | 0.931707 | 0.0793645- |
| chr1: 89575553-89575846.- | GBP2 | chr2: 191854400-191855953.- | STAT1 | 2.23167 | 0.590516 | 0.161414 |
| chr1: 89575553-89575846.- | GBP2 | chr17: 1543960-1546735.- | SCARF1 | 2.57631 | 0.728015 | 3.18144- |
| chr1: 89575553-89575846.- | GBP2 | chr1: 89528936-89530842.- | GBP1 | 2.55457 | 0.165796 | 0.471689- |
| chr1: 89575553-89575846.- | GBP2 | chr1: 89526007-89528727.- | GBP1 | 2.42901 | 0.18237 | 0.422759- |
| chr1: 89575553-89575846.- | GBP2 | chr1: 89522817-89523674.- | GBP1 | 2.34994 | 0.32477 | 0.207491 |
| chr1: 89575553-89575846.- | GBP2 | chr17: 56598521-56598614.- | SEPT4 | 2.4255 | 0.41128 | 2.01907 |
| chr1: 89575553-89575846.- | GBP2 | chr2: 191843727-191844497.- | STAT1 | 1.99444 | 0.796045 | 0.0476112 |
| chr1: 89575553-89575846.- | GBP2 | chr17: 1543036-1543205.- | SCARF1 | 2.56634 | 0.736768 | 2.17741- |
| chr1: 89575553-89575846.- | GBP2 | chr2: 191856046-191859786.- | STAT1 | 2.46696 | 0.414093 | 0.411724 |
| chr1: 89575553-89575846.- | GBP2 | chr2: 191844592-191845345.- | STAT1 | 1.89124 | 0.812357 | 0.325127 |
| chr1: 89575553-89575846.- | GBP2 | chr11: 57379409-57381800.+ | SERPING1 | 1.87954 | 0.32094 | 0.460319- |
| chr1: 89575553-89575846.- | GBP2 | chr1: 89726500-89727902.- | GBP5 | 1.56902 | 0.723535 | 0.225479 |
| chr1: 89520558-89520795.- | GBP1 | chr2: 191848466-191849035.- | STAT1 | 0.699666 | 1.36 | 1.84031 |
| chr1: 89520558-89520795.- | GBP1 | chr1: 89579979-89582674.- | GBP2 | 0.44283 | 2.13908 | 0.919959 |
| chr1: 89520558-89520795.- | GBP1 | chr2: 191844592-191845345.- | STAT1 | 0.824699 | 0.821144 | 2.28047 |
| chr1: 89520558-89520795.- | GBP1 | chr11: 57379409-57381800.+ | SERPING1 | 0.875861 | 0.435035 | 2.88972 |
| chr1: 89520558-89520795.- | GBP1 | chr1: 89575949-89578154.- | GBP2 | 0.557165 | 1.71068 | 0.365738 |
| chr11: 57374020-57379189.+ | SERPING1 | chr1: 89585971-89586825.- | GBP2 | 0.539517 | 1.20556 | 2.14247 |
| chr11: 57374020-57379189.+ | SERPING1 | chr11: 57373686-57373880.+ | SERPING1 | 0.92536 | 0.0298027 | 3.04264 |
| chr11: 57374020-57379189.+ | SERPING1 | chr2: 191854400-191855953.- | STAT1 | 0.781397 | 0.360227 | 2.87538 |
| chr11: 57374020-57379189.+ | SERPING1 | chr17: 56598521-56598614.- | SEPT4 | 0.808949 | 0.19628 | 3.87729 |
| chr11: 57374020-57379189.+ | SERPING1 | chr2: 191844592-191845345.- | STAT1 | 0.74879 | 0.455732 | 2.98671 |
| chr11: 57374020-57379189.+ | SERPING1 | chr1: 89575949-89578154.- | GBP2 | 0.535361 | 1.35973 | 1.40438 |
| chr11: 57374020-57379189.+ | SERPING1 | chr2: 191841751-191843581.- | STAT1 | 0.674327 | 0.75508 | 2.47148 |
| chr11: 57374020-57379189.+ | SERPING1 | chr1: 89573974-89575359.- | GBP2 | 0.562675 | 1.34835 | 1.46414 |
| chr1: 89525109-89525879.- | GBP1 | chr17: 1542220-1542932.- | SCARF1 | 1.0599 | 0.894694 | 5.73079 |
| chr1: 89525109-89525879.- | GBP1 | chr11: 57379409-57381800.+ | SERPING1 | 0.519001 | 0.536864 | 3.00322 |
| chr1: 89525109-89525879.- | GBP1 | chr1: 89575949-89578154.- | GBP2 | 0.485241 | 1.99697 | 0.569552 |
| chr17: 1542220-1542932.- | SCARF1 | chr11: 57373686-57373880.+ | SERPING1 | 0.696698 | 0.646829 | 4.50129 |
| chr17: 1542220-1542932.- | SCARF1 | chr2: 191848466-191849035.- | STAT1 | 0.867804 | 1.57137 | 3.9993 |
| chr17: 1542220-1542932.- | SCARF1 | chr1: 89579979-89582674.- | GBP2 | 0.638605 | 2.18914 | 2.67407 |
| chr17: 1542220-1542932.- | SCARF1 | chr2: 191844592-191845345.- | STAT1 | 0.964313 | 1.6562 | 5.55605 |
| chr17: 1542220-1542932.- | SCARF1 | chr1: 89575949-89578154.- | GBP2 | 0.828197 | 1.84588 | 2.55704 |
| chr11: 57373686-57373880.+ | SERPING1 | chr1: 89575949-89578154.- | GBP2 | 0.531271 | 1.3739 | 1.15453 |
| chr2: 191848466-191849035.- | STAT1 | chr1: 89573974-89575359.- | GBP2 | 1.4341 | 1.46236 | 0.430449 |

TABLE 2-continued

Junction PSVM.1 Model of 258 pairs from 63 unique gene product splice junctions representing products of 16 genes using normalised discriminants.

| Junction #1 | Gene #1 | Junction #2 | Gene #2 | Coefficient a | Coefficient b | Coefficient c |
|---|---|---|---|---|---|---|
| chr17: 1543960-1546735.- | SCARF1 | chr1: 89575949-89578154.- | GBP2 | 0.763275 | 2.50043 | 3.57916 |
| chr17: 1543960-1546735.- | SCARF1 | chr1: 89573974-89575359.- | GBP2 | 0.677217 | 2.26409 | 3.06968 |
| chr1: 89579979-89582674.- | GBP2 | chr1: 89522817-89523674.- | GBP1 | 2.25917 | 0.334777 | 0.905443 |
| chr1: 89579979-89582674.- | GBP2 | chr17: 56598521-56598614.- | SEPT4 | 2.29219 | 0.504063 | 3.67176 |
| chr1: 89579979-89582674.- | GBP2 | chr2: 191844592-191845345.- | STAT1 | 2.06935 | 0.74189 | 1.20385 |
| chr1: 89579979-89582674.- | GBP2 | chr11: 57379409-57381800.+ | SERPING1 | 1.94358 | 0.315178 | 1.31704 |
| chr1: 89522817-89523674.- | GBP1 | chr1: 89573974-89575359.- | GBP2 | 0.71785 | 1.83557 | 0.848872 |
| chr17: 56598521-56598614.- | SEPT4 | chr1: 89575949-89578154.- | GBP2 | 0.472098 | 2.25047 | 2.61309 |
| chr2: 191851794-191854340.- | STAT1 | chr11: 57379409-57381800.+ | SERPING1 | 1.16852 | 0.514826 | 3.86994 |
| chr2: 191856046-191859786.- | STAT1 | chr11: 57379409-57381800.+ | SERPING1 | 0.675213 | 0.614694 | 2.78033- |
| chr2: 191856046-191859786.- | STAT1 | chr1: 89575949-89578154.- | GBP2 | 0.538205 | 2.14412 | 0.0368301 |
| chr2: 191844592-191845345.- | STAT1 | chr11: 57379409-57381800.+ | SERPING1 | 1.06339 | 0.570523 | 3.25946 |
| chr11: 57379409-57381800.+ | SERPING1 | chr6: 36336848-36339106.- | ETV7 | 0.632268 | 0.326524 | 3.92187 |
| chr11: 57379409-57381800.+ | SERPING1 | chr1: 89575949-89578154.- | GBP2 | 0.42793 | 1.43736 | 1.00664 |
| chr11: 57379409-57381800.+ | SERPING1 | chr1: 89573974-89575359.- | GBP2 | 0.4849 | 1.4718 | 1.18336- |
| chr1: 89575949-89578154.- | GBP2 | chr1: 89726500-89727902.- | GBP5 | 1.43374 | 0.628899 | 0.115735- |
| chr1: 89573974-89575359.- | GBP2 | chr1: 89726500-89727902.- | GBP5 | 1.59502 | 0.721324 | 0.0499081 |

TABLE 3

48 unique primer probes and representative gene products used in PCR PSVM.1 model

| Gene | ABI primer |
|---|---|
| SEPT4 | Hs00910208_g1 |
| ANKRD22 | ANKRD22-j2 |
| APOL1 | Hs00358603_g1 |
| BATF2 | Hs00912736_m1 |
| ETV7 | ETV7-j2 |
| ETV7 | Hs00903228_m1 |
| ETV7 | Hs00903230_g1 |
| FCGR1A | Hs02340030_m1 |
| FCGR1B | Hs00417598_m1 |
| GBP1 | GBP1-j1 |
| GBP1 | Hs00266717_m1 |
| GBP1 | Hs00977005_m1 |
| GBP2 | GBP2-j1 |
| GBP2 | Hs00894837_m1 |
| GBP2 | Hs00894840_mH |
| GBP2 | Hs00894842_g1 |
| GBP2 | Hs00894846_g1 |
| GBP4 | Hs00925073_m1 |
| GBP5 | GBP5-j4 |
| GBP5 | Hs00369472_m1 |
| SCARF1 | Hs00186503_m1 |
| SCARF1 | Hs01092480_m1 |
| SCARF1 | Hs01092482_g1 |
| SCARF1 | Hs01092483_m1 |
| SCARF1 | Hs01092485_g1 |
| SERPING1 | Hs00163781_m1 |
| SERPING1 | Hs00934328_g1 |
| SERPING1 | Hs00934329_m1 |
| SERPING1 | Hs00934330_m1 |
| SERPING1 | Hs00935959_m1 |
| STAT1 | Hs01013989_m1 |
| STAT1 | Hs01013990_m1 |
| STAT1 | Hs01013991_m1 |
| STAT1 | Hs01013992_g1 |
| STAT1 | Hs01013993_m1 |
| STAT1 | Hs01013994_m1 |
| STAT1 | Hs01013995_g1 |
| STAT1 | Hs01013996_m1 |
| STAT1 | Hs01013997_m1 |
| STAT1 | Hs01013998_m1 |
| STAT1 | Hs01014000_m1 |
| STAT1 | Hs01014001_m1 |
| STAT1 | Hs01014002_m1 |
| STAT1 | Hs01014006_m1 |
| STAT1 | Hs01014008_m1 |
| TAP1 | Hs00388675_m1 |
| TAP1 | Hs00897093_g1 |
| TRAFD1 | Hs00938765_m1 |

TABLE 4

PCR PSVM.1 Model for 247 pairs using 48 unique gene primer and/or probe
sets representing products of 16 genes using normalised discriminants.

| Primer #1 | Primer #2 | Coefficient a | Coefficient b | Coefficient c |
|---|---|---|---|---|
| FCGR1C.Hs00417598_m1 | GBP2.Hs00894846_g1 | 0.989019 | 0.350334 | −0.0323861 |
| STAT1.Hs01014006_m1 | GBP2.Hs00894846_g1 | −0.00119499 | 2.00465 | −0.500782 |
| STAT1.Hs01014006_m1 | SCARF1.Hs01092483_m1 | −0.000571297 | 1.17195 | 5.41369 |
| GBP2-j1 | GBP1-j1 | 0.352167 | 1.21441 | 2.06111 |
| GBP2-j1 | STAT1.Hs01013997_m1 | 1.79145 | 0.690126 | 3.0344 |
| GBP2-j1 | SCARF1.Hs01092485_g1 | 2.20175 | −0.00171362 | −1.44567 |
| GBP2-j1 | STAT1.Hs01013994_m1 | 2.19993 | −0.00196353 | −1.3526 |
| GBP2-j1 | SERPING1.Hs00935959_m1 | 2.18284 | −0.00229246 | −1.26553 |
| GBP2-j1 | GBP1.Hs00977005_m1 | 0.484019 | 1.29118 | 0.255812 |
| GBP2-j1 | TAP1.Hs00897093_g1 | 1.09428 | 1.37719 | 0.471203 |
| GBP2-j1 | STAT1.Hs01013993_m1 | 0.719193 | 1.65117 | −0.646336 |
| GBP2-j1 | SERPING1.Hs00163781_m1 | 2.20741 | −0.00169947 | −1.44567 |
| GBP2-j1 | STAT1.Hs01013996_m1 | 0.847443 | 1.4461 | −1.39743 |
| GBP2-j1 | STAT1.Hs01014002_m1 | 0.217394 | 1.97095 | 1.38693 |
| GBP2-j1 | SERPING1.Hs00934329_m1 | 2.2842 | −0.00172007 | −1.54942 |
| GBP2-j1 | SCARF1.Hs01092483_m1 | 1.37914 | 0.695724 | 2.49551 |
| GBP2-j1 | SERPING1.Hs00934328_g1 | 2.20692 | −0.00170734 | −1.44096 |
| GBP2-j1 | STAT1.Hs01013995_g1 | 1.00587 | 1.07398 | −0.174949 |
| GBP2-j1 | STAT1.Hs01013990_m1 | 2.09844 | −0.000160377 | −1.29732 |
| GBP1-j1 | FCGR1C.Hs00417598_m1 | 0.715885 | 0.636782 | 1.43835 |
| GBP1-j1 | ETV7.Hs00903230_g1 | 1.32099 | 2.19E−05 | 2.11702 |
| GBP1-j1 | BATF2.Hs00912736_m1 | 1.33162 | −0.000456183 | 2.17523 |
| GBP1-j1 | GBP2.Hs00894837_m1 | 1.29776 | 0.214128 | 2.24112 |
| GBP1-j1 | STAT1.Hs01013994_m1 | 1.33121 | −0.000534804 | 2.20072 |
| GBP1-j1 | GBP1.Hs00977005_m1 | 0.686572 | 0.754215 | 1.55289 |
| GBP1-j1 | SERPING1.Hs00935959_m1 | 1.39539 | −0.000251084 | 2.25318 |
| GBP1-j1 | GBP1.Hs00977005_m1 | 0.711402 | 0.760907 | 1.59532 |
| GBP1-j1 | TAP1.Hs00897093_g1 | 1.14461 | 0.588754 | 2.64182 |
| GBP1-j1 | STAT1.Hs01013993_m1 | 0.922716 | 1.07963 | 1.61741 |
| GBP1-j1 | STAT1.Hs01013992_g1 | 1.02959 | 1.20584 | 10.0525 |
| GBP1-j1 | STAT1.Hs01013996_m1 | 1.12646 | 0.382193 | 1.77235 |
| GBP1-j1 | GBP1.Hs00977005_m1 | 0.690584 | 0.73865 | 1.5584 |
| GBP1-j1 | STAT1.Hs01014002_m1 | 0.576865 | 1.24859 | 2.02611 |
| GBP1-j1 | TRAFD1.Hs00938765_m1 | 1.32971 | −0.000488537 | 2.24776 |
| GBP1-j1 | GBP1.Hs00977005_m1 | 0.68678 | 0.754125 | 1.55323 |
| GBP1-j1 | FCGR1C.Hs00417598_m1 | 0.744211 | 0.589613 | 1.43788 |
| GBP1-j1 | GBP2.Hs00894846_g1 | 1.58338 | −0.43363 | 2.97581 |
| GBP1-j1 | GBP1.Hs00977005_m1 | 0.681074 | 0.749028 | 1.54319 |
| GBP1-j1 | GBP1.Hs00266717_m1 | 0.415366 | 0.90114 | 1.38866 |
| GBP1-j1 | SCARF1.Hs01092483_m1 | 0.974472 | 0.761654 | 5.34458 |
| GBP1-j1 | SERPING1.Hs00934328_g1 | 1.3859 | −0.000562151 | 2.40357 |
| GBP1-j1 | GBP1.Hs00266717_m1 | 0.415366 | 0.90114 | 1.38866 |
| GBP1-j1 | GBP2.Hs00894842_g1 | 1.19352 | 0.554055 | 2.76356 |
| GBP1-j1 | GBP1.Hs00266717_m1 | 0.415366 | 0.90114 | 1.38866 |
| GBP1-j1 | GBP1.Hs00977005_m1 | 0.690835 | 0.738909 | 1.55884 |
| GBP1-j1 | STAT1.Hs01013998_m1 | 1.13978 | 0.456745 | 3.04637 |
| GBP1-j1 | SERPING1.Hs00934330_m1 | −0.197036 | 1.0629 | 3.5301 |
| GBP1-j1 | ETV7.Hs00903228_m1 | 1.40817 | −0.000317355 | 2.22646 |
| GBP1-j1 | GBP2.Hs00894846_g1 | 1.58324 | −0.433587 | 2.97904 |
| GBP1-j1 | GBP2.Hs00894837_m1 | 1.31278 | 0.174194 | 2.26817 |
| SERPING1.Hs00934328_g1 | GBP2.Hs00894846_g1 | −0.00778095 | 2.45862 | −0.587509 |
| FCGR1C.Hs00417598_m1 | GBP2.Hs00894837_m1 | 0.895267 | 0.394906 | −0.179788 |
| ETV7.Hs00903230_g1 | GBP1.Hs00977005_m1 | −0.00217665 | 1.49226 | 0.632317 |
| ETV7.Hs00903230_g1 | TAP1.Hs00897093_g1 | −0.000231451 | 1.96472 | 1.09749 |
| ETV7.Hs00903230_g1 | GBP2.Hs00894846_g1 | −0.00114142 | 1.89327 | −0.40038 |
| ETV7.Hs00903230_g1 | GBP1.Hs00977005_m1 | −0.00217677 | 1.49226 | 0.632346 |
| ETV7.Hs00903230_g1 | GBP2.Hs00894842_g1 | −0.000467256 | 2.04153 | 1.74583 |
| ETV7.Hs00903230_g1 | STAT1.Hs01013998_m1 | −0.000949693 | 2.1619 | 4.26364 |
| ETV7.Hs00903230_g1 | SERPING1.Hs00934330_m1 | −0.00654176 | 0.943987 | 3.42896 |
| ETV7.Hs00903230_g1 | GBP2.Hs00894846_g1 | −0.00104398 | 1.89303 | −0.432454 |
| ETV7.Hs00903230_g1 | GBP2.Hs00894837_m1 | −0.00190538 | 2.53692 | −1.50499 |
| BATF2.Hs00912736_m1 | GBP2.Hs00894837_m1 | −0.00622887 | 2.63255 | −1.47972 |
| BATF2.Hs00912736_m1 | SERPING1.Hs00935959_m1 | −0.810593 | 0.811001 | −0.0452642 |
| BATF2.Hs00912736_m1 | GBP1.Hs00977005_m1 | −0.000915613 | 1.4944 | 0.898569 |
| BATF2.Hs00912736_m1 | GBP2.Hs00894846_g1 | −0.00718067 | 2.28481 | −0.6038 |
| BATF2.Hs00912736_m1 | GBP1.Hs00977005_m1 | −0.00041969 | 1.4942 | 0.651744 |
| BATF2.Hs00912736_m1 | STAT1.Hs01013998_m1 | −0.000142593 | 2.27113 | 4.39396 |
| BATF2.Hs00912736_m1 | SERPING1.Hs00934330_m1 | −0.000560179 | 0.96875 | 3.65037 |
| STAT1.Hs01013997_m1 | GBP2.Hs00894846_g1 | 0.790499 | 1.53954 | 4.30898 |
| STAT1.Hs01013997_m1 | SERPING1.Hs00934329_m1 | 1.21586 | −0.00197807 | 6.64929 |
| STAT1.Hs01013997_m1 | SCARF1.Hs01092483_m1 | 0.669806 | 1.25293 | 9.55564 |
| STAT1.Hs01013997_m1 | GBP2.Hs00894846_g1 | 0.780882 | 1.5423 | 4.26332 |
| STAT1.Hs01013997_m1 | GBP2.Hs00894837_m1 | 0.643309 | 1.582 | 2.84186 |
| GBP2.Hs00894837_m1 | GBP5.Hs00369472_m1 | 0.0793298 | 1.30149 | 0.807408 |
| GBP2.Hs00894837_m1 | GBP1.Hs00977005_m1 | 0.00513332 | 1.46086 | 0.607393 |

TABLE 4-continued

PCR PSVM.1 Model for 247 pairs using 48 unique gene primer and/or probe sets representing products of 16 genes using normalised discriminants.

| Primer #1 | Primer #2 | Coefficient a | Coefficient b | Coefficient c |
|---|---|---|---|---|
| GBP2.Hs00894837_m1 | SERPING1.Hs00163781_m1 | 2.75766 | −0.00550397 | −1.82782 |
| GBP2.Hs00894837_m1 | GBP1.Hs00977005_m1 | −0.0278154 | 1.49063 | 0.634159 |
| GBP2.Hs00894837_m1 | GBP1.Hs00977005_m1 | −0.0158235 | 1.47003 | 0.618179 |
| GBP2.Hs00894837_m1 | SERPING1.Hs00934329_m1 | 2.76608 | −0.00562398 | −1.88154 |
| GBP2.Hs00894837_m1 | GBP1.Hs00266717_m1 | 0.61853 | 1.04089 | 0.344154 |
| GBP2.Hs00894837_m1 | SERPING1.Hs00934328_g1 | 2.7701 | −0.00567224 | −1.86725 |
| GBP2.Hs00894837_m1 | STAT1.Hs01013990_m1 | 2.30134 | 0.000463346 | −1.55999 |
| GBP2.Hs00894837_m1 | STAT1.Hs01013991_m1 | 0.781252 | 1.64689 | 6.13806 |
| GBP2.Hs00894837_m1 | STAT1.Hs01013998_m1 | 0.681465 | 1.63497 | 2.94866 |
| GBP2.Hs00894837_m1 | SERPING1.Hs00934330_m1 | 0.0326647 | 0.913492 | 3.34614 |
| SCARF1.Hs01092485_g1 | SERPING1.Hs00935959_m1 | −0.934673 | 0.935864 | −0.559836 |
| SCARF1.Hs01092485_g1 | GBP1.Hs00977005_m1 | −0.000744747 | 1.49295 | 0.477514 |
| SCARF1.Hs01092485_g1 | STAT1.Hs01014002_m1 | −0.00494499 | 2.29056 | 1.60865 |
| SCARF1.Hs01092485_g1 | GBP1.Hs00977005_m1 | −0.000744739 | 1.49296 | 0.477516 |
| SCARF1.Hs01092485_g1 | GBP2.Hs00894846_g1 | −0.00759457 | 2.4408 | −0.638052 |
| SCARF1.Hs01092485_g1 | GBP2.Hs00894840_mH | 0.00823635 | 1.86305 | 0.572789 |
| SCARF1.Hs01092485_g1 | STAT1.Hs01013991_m1 | −0.00257158 | 2.04071 | 7.80503 |
| SCARF1.Hs01092485_g1 | STAT1.Hs01013998_m1 | −0.000256615 | 2.2355 | 4.28765 |
| SCARF1.Hs01092485_g1 | SERPING1.Hs00934330_m1 | 0.000652022 | 0.950186 | 3.26926 |
| SCARF1.Hs01092485_g1 | GBP2.Hs00894846_g1 | −0.00753147 | 2.44064 | −0.658691 |
| SCARF1.Hs01092485_g1 | GBP2.Hs00894837_m1 | −0.00558232 | 2.74026 | −1.76676 |
| STAT1.Hs01013994_m1 | GBP2.Hs00894846_g1 | −0.00784335 | 2.4421 | −0.548444 |
| STAT1.Hs01013994_m1 | SERPING1.Hs00934329_m1 | −0.995639 | 0.995671 | −0.0553233 |
| STAT1.Hs01013994_m1 | GBP2.Hs00894842_g1 | 0.0048842 | 2.19952 | 1.80511 |
| APOL1.Hs00358603_g1 | SERPING1.Hs00935959_m1 | −1.14922 | 1.14819 | 1.39316 |
| ETV7-j2 | STAT1.Hs01013992_g1 | 0.000285403 | 2.00562 | 12.8451 |
| ETV7-j2 | GBP2.Hs00894846_g1 | 0.00141785 | 1.9618 | −0.448292 |
| ETV7-j2 | STAT1.Hs01013995_g1 | 0.00118075 | 1.92092 | 0.51725 |
| ETV7-j2 | STAT1.Hs01013991_m1 | 0.00121742 | 1.88237 | 7.08852 |
| ETV7-j2 | STAT1.Hs01014000_m1 | −0.000379002 | 0.85608 | 2.03916 |
| ETV7-j2 | STAT1.Hs01013989_m1 | 0.00211765 | 2.23454 | 0.497817 |
| ETV7-j2 | STAT1.Hs01013998_m1 | 0.000366889 | 2.23313 | 4.44386 |
| ETV7-j2 | SERPING1.Hs00934330_m1 | 0.00174821 | 0.92526 | 3.16375 |
| ETV7-j2 | GBP2.Hs00894846_g1 | 0.0014391 | 1.96168 | −0.452391 |
| ETV7-j2 | GBP2.Hs00894837_m1 | 0.00144646 | 2.34469 | −1.55343 |
| GBP5.Hs00369472_m1 | TRAFD1.Hs00938765_m1 | 1.48794 | −0.00499303 | 0.765206 |
| GBP1.Hs00977005_m1 | TRAFD1.Hs00938765_m1 | 1.48185 | −0.0013725 | 0.629235 |
| GBP1.Hs00977005_m1 | GBP2.Hs00894846_g1 | 1.46138 | 0.0066525 | 0.601643 |
| GBP1.Hs00977005_m1 | SERPING1.Hs00934330_m1 | 0.217382 | 0.80812 | 3.08004 |
| GBP1.Hs00977005_m1 | GBP2.Hs00894846_g1 | 1.45455 | 0.0119276 | 0.596125 |
| SERPING1.Hs00935959_m1 | GBP1.Hs00977005_m1 | −0.000633011 | 1.48733 | 0.446955 |
| SERPING1.Hs00935959_m1 | TAP1.Hs00897093_g1 | 0.00648861 | 2.00369 | 1.12843 |
| SERPING1.Hs00935959_m1 | STAT1.Hs01013993_m1 | 0.00768731 | 2.13094 | −0.13722 |
| SERPING1.Hs00935959_m1 | GBP1.Hs00977005_m1 | −0.00078869 | 1.48887 | 0.486005 |
| SERPING1.Hs00935959_m1 | STAT1.Hs01014002_m1 | −0.00466933 | 2.34209 | 1.42726 |
| SERPING1.Hs00935959_m1 | GBP1.Hs00977005_m1 | −0.00078313 | 1.48925 | 0.484843 |
| SERPING1.Hs00935959_m1 | GBP4.Hs00925073_m1 | 0.000812403 | 0.411631 | 4.01694 |
| SERPING1.Hs00935959_m1 | GBP2.Hs00894846_g1 | −0.00895717 | 2.47597 | −0.251743 |
| SERPING1.Hs00935959_m1 | GBP1.Hs00977005_m1 | −0.000777427 | 1.48803 | 0.482792 |
| SERPING1.Hs00935959_m1 | GBP2.Hs00894840_mH | 0.00830331 | 1.8595 | 0.542081 |
| SERPING1.Hs00935959_m1 | GBP2.Hs00894842_g1 | 0.00435017 | 2.10208 | 1.87818 |
| SERPING1.Hs00935959_m1 | GBP1.Hs00266717_m1 | 0.00300687 | 1.38892 | 0.675534 |
| SERPING1.Hs00935959_m1 | GBP1.Hs00977005_m1 | −0.00063284 | 1.48751 | 0.447008 |
| SERPING1.Hs00935959_m1 | STAT1.Hs01014000_m1 | 0.000984581 | 0.963274 | 2.12935 |
| SERPING1.Hs00935959_m1 | ANKRD22-j2 | 0.499861 | −0.499175 | −0.711725 |
| SERPING1.Hs00935959_m1 | STAT1.Hs01013998_m1 | −0.000174791 | 2.16104 | 4.19628 |
| SERPING1.Hs00935959_m1 | GBP2.Hs00894846_g1 | −0.00817042 | 2.46277 | −0.432935 |
| SERPING1.Hs00935959_m1 | GBP2.Hs00894837_m1 | −0.00550264 | 2.76077 | −1.83478 |
| GBP1.Hs00977005_m1 | TAP1.Hs00897093_g1 | 1.27536 | 0.377286 | 0.8361 |
| GBP1.Hs00977005_m1 | STAT1.Hs01013996_m1 | 1.25943 | 0.451084 | 0.24101 |
| GBP1.Hs00977005_m1 | TRAFD1.Hs00938765_m1 | 1.48026 | −0.00137393 | 0.628665 |
| GBP1.Hs00977005_m1 | GBP2.Hs00894846_g1 | 1.46075 | 0.00705408 | 0.601277 |
| GBP1.Hs00977005_m1 | SERPING1.Hs00934328_g1 | 1.49352 | −0.00039948 | 0.310136 |
| GBP1.Hs00977005_m1 | GBP2.Hs00894842_g1 | 1.08296 | 0.548087 | 1.00402 |
| GBP1.Hs00977005_m1 | SCARF1.Hs01092482_g1 | 1.49276 | −0.000622713 | 0.447764 |
| GBP1.Hs00977005_m1 | STAT1.Hs01013998_m1 | 1.35875 | 0.230763 | 1.02931 |
| GBP1.Hs00977005_m1 | SERPING1.Hs00934330_m1 | 0.213767 | 0.809027 | 3.07878 |
| GBP1.Hs00977005_m1 | GBP2.Hs00894846_g1 | 1.49742 | 0.00660472 | 0.621739 |
| GBP1.Hs00977005_m1 | GBP2.Hs00894837_m1 | 1.49093 | −0.0194448 | 0.632467 |
| TAP1.Hs00897093_g1 | GBP2.Hs00894842_g1 | 1.6969 | 0.984753 | 2.30757 |
| TAP1.Hs00897093_g1 | SCARF1.Hs01092482_g1 | 2.01883 | 0.00601699 | 1.29774 |
| TAP1.Hs00897093_g1 | GBP2.Hs00894846_g1 | 1.49451 | 1.17671 | 1.01564 |
| TAP1.Hs00897093_g1 | GBP2.Hs00894837_m1 | 1.17228 | 1.40407 | 0.024899 |
| STAT1.Hs01013993_m1 | GBP2.Hs00894846_g1 | 1.67822 | 0.745805 | −0.355729 |
| STAT1.Hs01013993_m1 | SERPING1.Hs00934329_m1 | 2.11023 | 0.00904043 | −0.61956 |

TABLE 4-continued

PCR PSVM.1 Model for 247 pairs using 48 unique gene primer and/or probe sets representing products of 16 genes using normalised discriminants.

| Primer #1 | Primer #2 | Coefficient a | Coefficient b | Coefficient c |
|---|---|---|---|---|
| STAT1.Hs01013993_m1 | SCARF1.Hs01092483_m1 | 1.60095 | 0.712835 | 3.0216 |
| STAT1.Hs01013993_m1 | GBP2.Hs00894842_g1 | 2.12416 | 0.0562479 | −0.275739 |
| STAT1.Hs01013993_m1 | GBP2.Hs00894846_g1 | 1.68359 | 0.748191 | −0.355531 |
| STAT1.Hs01013993_m1 | GBP2.Hs00894837_m1 | 1.58676 | 1.20059 | −0.752196 |
| SERPING1.Hs00163781_m1 | GBP2.Hs00894846_g1 | −0.00799328 | 2.45956 | −0.54572 |
| SERPING1.Hs00163781_m1 | SERPING1.Hs00934329_m1 | −1.05423 | 1.0546 | −0.0277807 |
| SERPING1.Hs00163781_m1 | GBP2.Hs00894842_g1 | −0.00867745 | 2.45956 | −0.319761 |
| SERPING1.Hs00163781_m1 | GBP2.Hs00894837_m1 | −0.00551672 | 2.75772 | −1.82474 |
| SCARF1.Hs00186503_m1 | GBP2.Hs00894846_g1 | −0.00763942 | 2.43558 | −0.62241 |
| SCARF1.Hs00186503_m1 | GBP2.Hs00894842_g1 | 0.00483875 | 2.1899 | 1.80751 |
| STAT1.Hs01014008_m1 | SERPING1.Hs00934329_m1 | 1.13967 | 0.000308544 | 5.60475 |
| STAT1.Hs01014008_m1 | SERPING1.Hs00934330_m1 | 0.107219 | 0.911526 | 3.94125 |
| STAT1.Hs01013992_g1 | TRAFD1.Hs00938765_m1 | 2.13629 | −0.00402816 | 13.8002 |
| STAT1.Hs01013992_g1 | SERPING1.Hs00934330_m1 | 0.677802 | 0.817211 | 7.54728 |
| SERPING1.Hs00163781_m1 | GBP2.Hs00894846_g1 | −0.00863132 | 2.45949 | −0.334915 |
| SERPING1.Hs00163781_m1 | GBP2.Hs00894846_g1 | −0.0081476 | 2.45955 | −0.494743 |
| SERPING1.Hs00163781_m1 | GBP2.Hs00894837_m1 | −0.00551577 | 2.75772 | −1.82497 |
| STAT1.Hs01013996_m1 | GBP2.Hs00894846_g1 | 1.27751 | 1.00366 | −1.07206 |
| STAT1.Hs01013996_m1 | GBP2.Hs00894846_g1 | 1.30027 | 1.03125 | −1.08777 |
| STAT1.Hs01013996_m1 | GBP2.Hs00894837_m1 | 1.19853 | 1.26855 | −1.54265 |
| GBP1.Hs00977005_m1 | GBP2.Hs00894846_g1 | 1.4678 | 0.00520348 | 0.606082 |
| GBP1.Hs00977005_m1 | SERPING1.Hs00934329_m1 | 1.49377 | −0.000452579 | 0.326644 |
| FCGR1A.Hs02340030_m1 | GBP2.Hs00894846_g1 | −1.71E−05 | 1.59565 | −0.357857 |
| STAT1.Hs01014002_m1 | SERPING1.Hs00934329_m1 | 2.33494 | −0.00466771 | 1.43162 |
| STAT1.Hs01014002_m1 | SCARF1.Hs01092483_m1 | 1.67591 | 0.58036 | 3.94163 |
| STAT1.Hs01014002_m1 | SERPING1.Hs00934330_m1 | 1.22081 | 0.586378 | 3.24649 |
| STAT1.Hs01014002_m1 | ETV7.Hs00903228_m1 | 2.39641 | −0.00498453 | 1.66378 |
| STAT1.Hs01014002_m1 | GBP2.Hs00894846_g1 | 1.98637 | 0.154864 | 1.48806 |
| TRAFD1.Hs00938765_m1 | GBP1.Hs00977005_m1 | −0.00134843 | 1.47187 | 0.61818 |
| TRAFD1.Hs00938765_m1 | SERPING1.Hs00934329_m1 | −1.12124 | 1.11893 | 2.68837 |
| TRAFD1.Hs00938765_m1 | GBP1.Hs00266717_m1 | 0.00273817 | 1.37928 | 0.724895 |
| TRAFD1.Hs00938765_m1 | STAT1.Hs01013995_g1 | 0.00712533 | 1.68753 | 0.478541 |
| TRAFD1.Hs00938765_m1 | GBP2.Hs00894842_g1 | 0.00329211 | 2.14786 | 2.1722 |
| TRAFD1.Hs00938765_m1 | STAT1.Hs01013998_m1 | −0.000504025 | 2.1598 | 4.27616 |
| TRAFD1.Hs00938765_m1 | SERPING1.Hs00934330_m1 | −0.0629882 | 0.94911 | 3.41863 |
| TRAFD1.Hs00938765_m1 | GBP2.Hs00894846_g1 | −0.00772786 | 2.42651 | −0.555942 |
| TRAFD1.Hs00938765_m1 | GBP5-j4 | −0.00224535 | 1.42678 | 0.826857 |
| GBP1.Hs00977005_m1 | GBP2.Hs00894846_g1 | 1.45508 | 0.011358 | 0.598166 |
| GBP1.Hs00977005_m1 | SERPING1.Hs00934329_m1 | 1.49369 | −0.00043339 | 0.320276 |
| GBP1.Hs00977005_m1 | GBP2.Hs00894842_g1 | 1.09574 | 0.583467 | 1.03006 |
| GBP1.Hs00977005_m1 | GBP2.Hs00894846_g1 | 1.47157 | 0.0111962 | 0.610537 |
| GBP1.Hs00977005_m1 | GBP2.Hs00894837_m1 | 1.47924 | −0.00143613 | 0.620878 |
| GBP2.Hs00894846_g1 | GBP1.Hs00977005_m1 | 0.0121025 | 1.45439 | 0.597851 |
| GBP2.Hs00894846_g1 | SERPING1.Hs00934329_m1 | 2.45775 | −0.00759428 | −0.664409 |
| GBP2.Hs00894846_g1 | TAP1.Hs00388675_m1 | 1.37355 | 0.923528 | 0.16456 |
| GBP2.Hs00894846_g1 | GBP1.Hs00266717_m1 | 0.392356 | 1.16601 | 0.765801 |
| GBP2.Hs00894846_g1 | SCARF1.Hs01092483_m1 | 0.804906 | 0.943157 | 4.20691 |
| GBP2.Hs00894846_g1 | SERPING1.Hs00934328_g1 | 2.45867 | −0.00779154 | −0.515874 |
| GBP2.Hs00894846_g1 | STAT1.Hs01013995_g1 | 1.01781 | 1.09662 | 0.300605 |
| GBP2.Hs00894846_g1 | STAT1.Hs01013990_m1 | 2.08134 | 0.000148481 | −0.579165 |
| GBP2.Hs00894846_g1 | GBP1.Hs00266717_m1 | 0.392352 | 1.166 | 0.765789 |
| GBP2.Hs00894846_g1 | GBP1.Hs00266717_m1 | 0.381078 | 1.17719 | 0.771042 |
| GBP2.Hs00894846_g1 | GBP1.Hs00977005_m1 | 0.00894593 | 1.47941 | 0.611006 |
| GBP2.Hs00894846_g1 | SEPT4.Hs00910208_g1 | 2.42651 | −0.00796056 | −0.438044 |
| GBP2.Hs00894846_g1 | STAT1.Hs01014000_m1 | 1.83002 | 0.585907 | 1.30532 |
| GBP2.Hs00894846_g1 | SCARF1.Hs01092482_g1 | 2.4409 | −0.00761351 | −0.628835 |
| GBP2.Hs00894846_g1 | STAT1.Hs01013989_m1 | −0.243619 | 2.34986 | 0.887395 |
| GBP2.Hs00894846_g1 | STAT1.Hs01013998_m1 | 0.755166 | 1.50715 | 3.02742 |
| GBP2.Hs00894846_g1 | SERPING1.Hs00934330_m1 | −0.107372 | 0.989441 | 3.67548 |
| GBP2.Hs00894846_g1 | GBP5-j4 | −0.0211427 | 1.43378 | 1.0599 |
| GBP1.Hs00977005_m1 | STAT1.Hs01013995_g1 | 1.22344 | 0.420315 | 0.685002 |
| GBP1.Hs00977005_m1 | GBP2.Hs00894842_g1 | 1.08304 | 0.548068 | 1.00401 |
| GBP1.Hs00977005_m1 | STAT1.Hs01013998_m1 | 1.35851 | 0.230722 | 1.02919 |
| GBP1.Hs00977005_m1 | SERPING1.Hs00934330_m1 | 0.216417 | 0.808309 | 3.07918 |
| GBP1.Hs00977005_m1 | GBP2.Hs00894846_g1 | 1.48007 | 0.00576588 | 0.615471 |
| SERPING1.Hs00934329_m1 | GBP2.Hs00894840_mH | 0.00892279 | 1.97902 | 0.59293 |
| SERPING1.Hs00934329_m1 | SERPING1.Hs00934328_g1 | 0.923962 | −0.925328 | 0.647415 |
| SERPING1.Hs00934329_m1 | SEPT4.Hs00910208_g1 | 0.932037 | −0.92973 | −2.00257 |
| SERPING1.Hs00934329_m1 | STAT1.Hs01013998_m1 | −0.000346258 | 2.11283 | 4.08355 |
| SERPING1.Hs00934329_m1 | GBP2.Hs00894846_g1 | −0.00758256 | 2.4577 | −0.668225 |
| SERPING1.Hs00934329_m1 | STAT1.Hs01014001_m1 | −0.00175861 | 2.1082 | 2.53692 |
| SERPING1.Hs00934329_m1 | GBP2.Hs00894837_m1 | −0.00562271 | 2.76607 | −1.88195 |
| GBP1.Hs00266717_m1 | SCARF1.Hs01092483_m1 | 1.08049 | 0.787208 | 4.44797 |
| GBP1.Hs00266717_m1 | SERPING1.Hs00934330_m1 | 0.189414 | 0.815617 | 3.14513 |
| GBP1.Hs00266717_m1 | GBP2.Hs00894846_g1 | 1.16599 | 0.392351 | 0.765784 |

TABLE 4-continued

PCR PSVM.1 Model for 247 pairs using 48 unique gene primer and/or probe sets representing products of 16 genes using normalised discriminants.

| Primer #1 | Primer #2 | Coefficient a | Coefficient b | Coefficient c |
|---|---|---|---|---|
| SCARF1.Hs01092483_m1 | SERPING1.Hs00934328_g1 | 1.17296 | −0.00065024 | 5.05175 |
| SCARF1.Hs01092483_m1 | STAT1.Hs01013995_g1 | 0.818695 | 1.24316 | 4.26207 |
| SCARF1.Hs01092483_m1 | GBP2.Hs00894842_g1 | 0.813532 | 1.25883 | 4.94645 |
| SCARF1.Hs01092483_m1 | STAT1.Hs01013998_m1 | 0.891858 | 1.3931 | 7.07665 |
| SCARF1.Hs01092483_m1 | GBP2.Hs00894846_g1 | 0.962467 | 0.821385 | 4.3109 |
| SERPING1.Hs00934328_g1 | GBP2.Hs00894846_g1 | −0.00779865 | 2.4587 | −0.51415 |
| STAT1.Hs01013995_g1 | GBP2.Hs00894837_m1 | 0.912586 | 1.47967 | −0.432093 |
| GBP2.Hs00894842_g1 | GBP1.Hs00977005_m1 | 0.58192 | 1.10695 | 1.03815 |
| GBP2.Hs00894842_g1 | SEPT4.Hs00910208_g1 | 2.22843 | −0.000262976 | 1.94752 |
| GBP2.Hs00894842_g1 | STAT1.Hs01013998_m1 | 0.847927 | 1.34927 | 3.68526 |
| GBP2.Hs00894842_g1 | SERPING1.Hs00934330_m1 | 0.178795 | 0.841153 | 3.25947 |
| GBP1.Hs00977005_m1 | GBP2.Hs00894837_m1 | 1.47803 | −0.0085356 | 0.621696 |
| SEPT4.Hs00910208_g1 | GBP2.Hs00894846_g1 | −0.00765387 | 2.42183 | −0.50983 |
| STAT1.Hs01013991_m1 | SERPING1.Hs00934330_m1 | 0.142577 | 0.878605 | 3.80188 |
| STAT1.Hs01013989_m1 | SERPING1.Hs00934330_m1 | 0.555923 | 0.664478 | 2.71143 |
| STAT1.Hs01013989_m1 | GBP2.Hs00894846_g1 | 2.3479 | −0.220153 | 0.892446 |
| STAT1.Hs01013998_m1 | SERPING1.Hs00934330_m1 | 0.172006 | 0.863022 | 3.56453 |
| SERPING1.Hs00934330_m1 | ETV7.Hs00903228_m1 | 0.893693 | −0.000307422 | 3.26652 |
| SERPING1.Hs00934330_m1 | GBP2.Hs00894846_g1 | 0.965934 | −0.0986572 | 3.56846 |
| SERPING1.Hs00934330_m1 | GBP2.Hs00894837_m1 | 0.91319 | 0.0333932 | 3.34469 |
| GBP2.Hs00894846_g1 | GBP5-j4 | 0.0288874 | 1.3975 | 1.03954 |
| GBP2.Hs00894837_m1 | GBP5-j4 | 0.117087 | 1.3916 | 0.983624 |

TABLE 5

Custom primer chromosomal locations and product transcript sequences unique used in the PCR 16-gene model. All commercially available TaqMan primers are available off-shelf from ThermoFisherScientific (www.thermofisher.com).

| Custom primer | Chromosomal location | Exon numbers in transcript Left exon | Right exon | Exon number, relative to 5' Left exon | right exon | NCBI gene reference | Transcript Sequence |
|---|---|---|---|---|---|---|---|
| ETV7-j2 | chr6: 36322464-36334651 | 8 | 7 | 1 | 3 | NM_001207035 | SEQ ID NO: 1 AACCGGGTGAACATGACCTAC GAGAAGATGTCTCGTGCCCTG CGCCACTATTATAAGCTTAATA TCATTAAGAAGGAACCGGGGC AGAAACTCCTGTTCAGAAATG GACTTCAGCTGATCTTCATATT CATATGGAGTTTCCAGTGACC CCAAATAGCCAAAACAGTCTT GGAAAGAAAAACAAAGTTGGA GGACCCACACTTCCTGATTTT GAAACTTGCTACAAAGCTATA GTACTCAACAAAGATTGGTAA TGGCATAAGGATATAGATTAA GAACAGTTTTTTCAACAAATAG TGTTGGGACAATGGGTGTCCA CATGCAAAAGAATAAAGTTGT CCCCTTACCTTACACCATCTC CAAAAATTAACTCAAAATATGT CAAAGACATAAACGTAAGAGC TAAAACTGTAAAACTCCTAGAA TAAAACATAGGAGTAAATCTTC ATGACCTTGGATTAGGCCATT GTGTCTTAAATATAACACCAAA AGAATAAGTAATAAAAAAATAG ATAAATTGAACTCCATCAAAAT TAAAAGCCTTTGTGCTTCATA GGACACCATCAAG |
| GBP1-j1 | chr1: 89523917-89524523 | 6 | 5 | 6 | 7 | NM_002053 | SEQ ID NO: 2 CTATGTGACAGAGCTGACACA TAGAATCCGATCAAAATCCTC ACCTGATGAGAATGAGAATGA GGTTGAGGATTCAGCTGACTT TGTGAGCTTCTTCCCAGACTT TGTGTGGACACTGAGAGATTT CTCCCTGGACTTGGAAGCAGA |

TABLE 5-continued

Custom primer chromosomal locations and product transcript sequences unique used in the PCR 16-gene model. All commercially available TaqMan primers are available off-shelf from ThermoFisherScientific (www.thermofisher.com).

| Custom primer | Chromosomal location | Exon numbers in transcript | | Exon number, relative to 5' NCBI | | gene reference | Transcript Sequence |
|---|---|---|---|---|---|---|---|
| | | Left exon | Right exon | Left exon | right exon | | |
| | | | | | | | TGGACAACCCCTCACACCAGA TGAGTACCTGACATACTCCCT GAAGCTGAAGAAAGGTACCAG TCAAAAAGATGAAACTTTTAAC CTGCCCAGACTCTGTATCCGG AAATTCTTCCCAAAGAAAAAAT GCTTTGTCTTTGATCGGCCCG TTCACCGCAGGAAGCTTGCCC AGCTCGAGAAACTACAAGATG AAGAGCTGGACCCCGAATTTG TGCAACAAGTAGCAGACTTCT GTTCCTACATCTTTAGTAATTC CAAAACTAAAACTCTTTCAGG AGGCATCCAGGTCAACGGGC CTC |
| GBP2-j1 | chr1: 89578367-89579698 | 8 | 7 | 4 | 5 | NM_004120 | SEQ ID NO: 3 GTCTAGAGAGCCTGGTGCTGA CCTACGTCAATGCCATCAGCA GTGGGGATCTACCCTGCATG GAGAACGCAGTCCTGGCCTT GGCCCAGATAGAGAACTCAG CCGCAGTGGAAAGGCTATTG CCCACTATGAACAGCAGATGG GCCAGAAGGTGCAGCTGCCC ACGGAAACCCTCCAGGAGCT GCTGGACCTGCACAGGGACA GTGAGAGAGAGGCCATTGAA GTCTTCATGAAGAACTCTTTCA AGGATGTGGACCAAATGTTCC AGAGGAAATTAGGGGCCCAG TTGGAAGCAAGGCGAGATGA CTTTTGTAAGCAGAATTCCAAA GCATCATCAGATTGTTGCATG GCTTTACTTCAGGATATATTTG GCCCTTTAGAAGAAGATGTCA AGCAGGGAACATTTTCTAAAC CAGGAGGTTACCGTCTCTTTA CTCAGAAGCTGCAGGAGCTG AAGAATAAGTACTACCAGGTG CCAAGGAAGGGGATACAG |
| GBP5-j4 | chr1: 89726500-89727902 | 12 | 11 | 1 | 2 | NM_052942 | SEQ ID NO: 4 AGGCACAAGTGAAAGCAGAA GCTGAAAAGGCTGAAGCGCA AAGGTTGGCGGCGATTCAAAG GCAGAACGAGCAAATGATGCA GGAGAGGGAGAGACTCCATC AGGAACAAGTGAGACAAATGG AGATAGCCAAACAAAATTGGC TGGCAGAGCAACAGAAAATGC AGGAACAACAGATGCAGGAAC AGGCTGCACAGCTCAGCACAA CATTCCAAGCTCAAAATAGAA GCCTTCTCAGTGAGCTCCAGC ACGCCCAGAGGACTGTTAATA ACGATGATCCATGTGTTTTACT CTAAAGTGCTAAATATGGGAG TTTCCTTTTTTTACTCTTTGTC ACTGATGACACAACAGAAAAG AAACTGTAGACCTTGGGACAA TCAACATTTAAATAAACTTTAT AATTATTTTTCAAACTTTCATA TAGAGTTATAAGATTATGATGC TGGTATCTGGTAAAATGTACA TCCCAGTAGTCCAATAGTTTA AATGTTATTGCTTCCTTTAAG AGATTATAAATTGTATAAGGGA CATTGTATCACTGCCTTCATTT ATGCGTGATATTGGGATGGTT |

TABLE 5-continued

Custom primer chromosomal locations and product transcript sequences unique used in the PCR 16-gene model. All commercially available TaqMan primers are available off-shelf from ThermoFisherScientific (www.thermofisher.com).

| Custom primer | Chromosomal location | Exon numbers in transcript | | Exon number, relative to 5' NCBI | | gene reference | Transcript Sequence |
|---|---|---|---|---|---|---|---|
| | | Left exon | Right exon | Left exon | right exon | | |
| | | | | | | | TCATCAGGAGATGCTTTCCTT |
| | | | | | | | GCATCTCAATGTCATCTGTCT |
| | | | | | | | AATTTCTCATAAGGGGATTAT |
| | | | | | | | GTTACCTAGAGCAGGGCTTCC |
| | | | | | | | CAACCCTCAGGCCATAGACTA |
| | | | | | | | GCTCTGATCTGTGGCCTCTTA |
| | | | | | | | GGAACCCGGCCACACAGCAG |
| | | | | | | | GAGGTGAGCAGCAGGTAAGT |
| | | | | | | | GAGCATTACAGCCTGAGCTCC |
| | | | | | | | ACCTCCTGTCAGATCAGCAGT |
| | | | | | | | GACATTAGATTCTCACAGGAG |
| | | | | | | | TGGGAACCCTATTGTGAACTG |
| | | | | | | | TGCATGCAAAAGATCTAGGTT |
| | | | | | | | GTGTGATCCTTGTGGAACAAT |
| | | | | | | | ATAAACCAGAAACCAATAACG |
| | | | | | | | CCACCCCACCTCCAACCCCC |
| | | | | | | | GCCAACCCTCTGTGGAAAAAT |
| | | | | | | | TACCTTCCACGAAACTGGTCC |
| | | | | | | | CTGATGCCAAATAGGTTGGGG |
| | | | | | | | GACCGCTGACCTAGAGGGAG |
| | | | | | | | TTATGCACATGGGCTTATAAG |
| | | | | | | | GTTAGCCAAGAGAAAGGACAA |
| | | | | | | | GAAGACCCAAAGTCGGCAAG |
| | | | | | | | CAAATTTATTAACCTGCTGGG |
| | | | | | | | CTGCTCTACAGAAATCTGAGG |
| | | | | | | | AGGCAGACACCGGCTTACA |
| | | | | | | | GGCTAAGGGGTATAAGTAGGT |
| | | | | | | | CTGCAGGGGTTTTGTGTGTGT |
| | | | | | | | GTGCGGGGGTGTCGGGGGG |
| | | | | | | | GCAAGGCCATTTGTGGAGACT |
| | | | | | | | TTTCCTCCCAGTATGGCCACA |
| | | | | | | | TCCTGCAGTTTGTCAGTTTTTG |
| | | | | | | | CCCCCGCCTGGCTCAGGGTA |
| | | | | | | | CCAGGATGTGGTTTAGCTTAG |
| | | | | | | | GGGTGGTTATAGTGGCACCTA |
| | | | | | | | AGTTCTGGGAACTTGCGGTGG |
| | | | | | | | GGGCGACCTTTTGGACGAAAA |
| | | | | | | | ATAAGCTGCAGGGCAGCTAG |
| | | | | | | | GGGAGGGGGCTTGTTATATTC |
| | | | | | | | CTCTGGGGGCAGGGTGTCCC |
| | | | | | | | TAACTGGGCTCAGTCGGAAG |
| | | | | | | | GAACTTGACCAAAGTCTGGGC |
| | | | | | | | TCAGTTGGGCATCACTCAGGC |
| | | | | | | | TAATGGTCGTGTGCTGGATGC |
| | | | | | | | CATCAGAGGGAAGTACCAATG |
| | | | | | | | GTAAAGTGGAAACAATGTGCA |
| | | | | | | | GCTTTCAACTGGGTGGAGGCT |
| | | | | | | | GCTATTCTGTGGACAGTGAGA |
| | | | | | | | TGTTTCCTTGGCACTGTCAAT |
| | | | | | | | AGACAATCTGCGTAGAGAAAT |
| | | | | | | | TCCAAGCTGAAAGCCAATAAT |
| | | | | | | | GTTATAATAAAATAGAGATTCT |
| | | | | | | | TCAGAAGATGAAAGGAATTAC |
| | | | | | | | CAGCATGGAAATTGTGTCATA |
| | | | | | | | GGCTTAAGGGCTAAAGAAGAA |
| | | | | | | | GCCTTTTCTTTTCTGTTCACCC |
| | | | | | | | TCACCAAGAGCACAACTTAAA |
| | | | | | | | TAGGGCATTTTATAACCTGAA |
| | | | | | | | CACAATTTATATTGGACTTAAT |
| | | | | | | | TATTATGTGTAATATGTTTATA |
| | | | | | | | ATCCTTTAGATCTTATAAATAT |
| | | | | | | | GTGGTATAAGGAATGCCATAT |
| | | | | | | | AATGTGCCAAAAATCTGAGTG |
| | | | | | | | CATTTAATTTAATGCTTGCTTA |
| | | | | | | | TAGTGCTAAAGTTAAATGATCT |
| | | | | | | | TAATTCTTTGCAATTATATATG |
| | | | | | | | AAAAATGACTGATTTTTCTTAA |
| | | | | | | | AATATGTAACTTATATAAATAT |
| | | | | | | | ATCTGTTTGTACAGATTTTAAC |

TABLE 5-continued

Custom primer chromosomal locations and product transcript sequences unique used in the PCR 16-gene model. All commercially available TaqMan primers are available off-shelf from ThermoFisherScientific (www.thermofisher.com).

| Custom primer | Chromosomal location | Exon numbers in transcript Left exon | Right exon | Exon number, relative to 5' NCBI Left exon | right exon | gene reference | Transcript Sequence |
|---|---|---|---|---|---|---|---|
| | | | | | | | CATAAAAACATTTTTGGAAAAC CATAAA |

TABLE 6

6 unique primer probes and representative gene products used in PCR 6-gene model

| Gene | ABI primer |
|---|---|
| GBP2 | Hs00894846_g1 |
| FCGR1B | Hs02341825_m1 |
| SERPING1 | Hs00934329_m1 |
| TUBGCP6 | Hs00363509_g1 |
| TRMT2A | Hs01000041_g1 |
| SDR39U1 | Hs01016970_g1 |

TABLE 7

PCR 6-gene model, for 9 pairs using 6 unique gene primer and/or probe sets representing products of 6 genes.

| Primer #1 | Primer #2 | Coefficient d |
|---|---|---|
| GBP2.Hs00894846_g1 | TUBGCP6.Hs00363509_g1 | −2.3 |
| GBP2.Hs00894846_g1 | TRMT2A.Hs01000041_g1 | −5.7 |
| GBP2.Hs00894846_g1 | SDR39U1.Hs01016970_g1 | −4.7 |
| FCGR1B.Hs02341825_m1 | TUBGCP6.Hs00363509_g1 | 2.4 |
| FCGR1B.Hs02341825_m1 | TRMT2A.Hs01000041_g1 | −1.2 |
| FCGR1B.Hs02341825_m1 | SDR39U1.Hs01016970_g1 | −0.2 |
| SERPING1.Hs00934329_m1 | TUBGCP6.Hs00363509_g1 | 0.7 |
| SERPING1.Hs00934329_m1 | TRMT2A.Hs01000041_g1 | −2.5 |
| SERPING1.Hs00934329_m1 | SDR39U1.Hs01016970_g1 | −1.5 |

TABLE 8

Reference gene product splice junctions used to normalise data for Junction PSVM.1 model.

| Junction | Gene |
|---|---|
| chr12: 50149538-50152009.+ | TMBIM6 |
| chr12: 50152263-50152465.+ | TMBIM6 |
| chr12: 50152545-50153003.+ | TMBIM6 |
| chr12: 50152058-50152165.+ | TMBIM6 |
| chr1: 115261366-115262199.− | CSDE1 |
| chr1: 22413359-22417920.+ | CDC42 |
| chr1: 154130197-154142875.− | TPM3 |
| chr11: 67050699-67051177.+ | ADRBK1 |
| chr11: 67051844-67052317.+ | ADRBK1 |
| chr1: 115262363-115263159.− | CSDE1 |
| chr19: 35761500-35761620.+ | USF2 |
| chr2: 114713283-114714936.+ | ACTR3 |
| chr2: 158272655-158275034.− | CYTIP |
| chr5: 176778292-176778452.− | LMAN2 |
| chr5: 176859807-176860147.+ | GRK6 |
| chr1: 154142945-154143124.− | TPM3 |
| chr5: 176764786-176765488.− | LMAN2 |
| chr12: 50153104-50155486.+ | TMBIM6 |
| chr1: 115260837-115261233.− | CSDE1 |
| chr5: 176765606-176778173.− | LMAN2 |

TABLE 9

Reference primers used to normalise data for PCR PSVM.1 model.

ACTR3.Hs01029159_g1
ADRBK1.Hs01056345_g1
CDC42.Hs03044122_g1
CSDE1.Hs00918650_m1
CYTIP.Hs00188734_m1
TMBIM6.Hs01012081_m1
TMBIM6.Hs00162661_m1
TMBIM6.Hs01012082_g1
TPM3.Hs01900726_g1
USF2.Hs01100994_g1

TABLE 10

Model performance statistics.

| | ACS | | MRC | | SUN | | AHRI | |
|---|---|---|---|---|---|---|---|---|
| Junction | AUC | P-value | AUC | P-value | AUC | P-value | AUC | P-value |
| PSVM.1 | 0.74 | NA (5-fold CV) | 0.67 | 4.1E−04 | 0.76 | 8.7E−08 | 0.63 | 0.082 |
| PCR PSVM.1 | 0.7 | 1.10E−08 | 0.67 | 3.4E−04 | 0.71 | 4.5E−06 | * | * |
| PCR 6-gene | 0.69 | 2.8E−08 | 0.71 | 2.2E−05 | 0.71 | 6.9E−06 | 0.68 | 2.45E−02 |

ACS = adolescent cohort study, which was used to develop the models and assign the coefficients.
MRC, SUN, and AHRI represent the Gambian, South Africa, and Ethiopian cohorts, respectively, from the GC6-74 adult household contact progressor study.
*PCR PSVM.1 not tested in AHRI samples.

The invention will be described by way of the following example which is not to be construed as limiting in any way the scope of the invention.

EXAMPLES

Methods
Cohorts and Blood Collection

Participants from the South African adolescent cohort study (ACS) were evaluated to identify and validate prospective signatures of risk of tuberculosis disease (FIG. 1A). The ACS determined the prevalence and incidence of tuberculosis infection and disease among adolescents from the Cape Town region of South Africa (Mahomed, Hawkridge et al. 2011, Mahomed, Ehrlich et al. 2013). A total of 6,363 healthy adolescents, aged 12 to 18 years, were enrolled. Approximately 50% of participants were evaluated at enrolment and every 6 months during 2 years of follow-up; others were evaluated at baseline and at 2 years. At enrolment and at each visit, clinical data were collected, and 2.5 mL blood drawn directly into PAXgene blood RNA tubes (PreAnalytiX); PAXgene tubes were stored at −20° C.

In addition, participants from the Grand Challenges 6-74 Study (GC6-74) were studied to independently validate signatures of risk (FIG. 1B). A total of 4,466 healthy, HIV negative persons aged 10 to 60 years, who had household exposure to an adult with sputum smear positive tuberculosis disease, were enrolled. Sites in South Africa (SUN), the Gambia (MRC), Ethiopia (AHRI) and Uganda participated. At baseline and at 6 months (the Gambia only) and at 18 months (all sites), participants were evaluated clinically and blood was collected directly into PAXgene tubes; these tubes were stored at −20 QC. Follow-up continued for a total of 2 years.

The study protocols were approved by relevant human research ethics committees. Written informed consent was obtained from participants. For adolescents, consent was obtained from parents or legal guardians of adolescents, and written informed assent from each adolescent.
Definition of Cases and Controls for Identifying and Validating Signatures of Tuberculosis Risk For the ACS signatures of risk study, adolescents with latent tuberculosis infection at enrolment were eligible; tuberculosis infection was diagnosed by a positive QuantiFERON® TB GOLD In-Tube Assay (OFT®, Cellestis; >0.35 IU/mL) and/or a positive tuberculin skin test (TST, 0.1 mL dose of Purified Protein Derivative RT-23, 2-TU, Staten Serum Institute; >10 mm). Overall, 53% of ACS participants had latent tuberculosis infection at enrolment. OFT® and/or TST positive adolescents were not given therapy to prevent TB disease, as South African tuberculosis management guidelines reserve this intervention for young children and HIV-infected persons.

Adolescents who developed active tuberculosis disease during follow up were included in the case control study as "progressors" (cases). Participants that were either exposed to tuberculosis patients, or had symptoms suggestive of tuberculosis, were evaluated clinically and by sputum smear, culture and chest roentgenography. Tuberculosis was defined as intrathoracic disease, with either two sputum smears positive for acid-fast bacilli or one positive sputum culture confirmed as *Mycobacterium tuberculosis* complex (mycobacterial growth indicator tube, MGIT, BD BioSciences). Participants who were not infected with tuberculosis at enrolment, but who developed tuberculosis disease and had converted to a positive QFT and/or TST at least 6 months prior to this diagnosis, were also included as progressors. For each progressor, two matched controls were identified. Controls were selected from ACS participants that remained healthy for the two years of follow up, and were matched to progressors by age at enrolment, gender, ethnicity, school of attendance, and presence or absence of prior episode of tuberculosis disease.

For the case control study, participants were excluded if they developed tuberculosis disease within 6 months of enrolment, or if they were HIV infected; all patients with tuberculosis disease were offered a HIV test, but some refused to be tested. HIV testing of healthy study participants was not permitted by the human research ethics committee of the University of Cape Town; this committee also did not allow post-hoc, anonymous HIV testing. Regardless, the HIV incidence rate in adolescents diagnosed with active tuberculosis was <2% (1 out of 61 who were offered and accepted testing), and since HIV is a risk factor for tuberculosis, we expect the HIV prevalence among healthy adolescents (from whom controls were identified) to be negligible.

Among GC6-74 participants, progressors had intrathoracic tuberculosis, defined in one of three ways. First, two positive sputum cultures (MGIT); second, one positive sputum culture and/or a positive sputum smear, and clinical signs and symptoms compatible with tuberculosis and/or a chest roentgenogram compatible with active pulmonary tuberculosis; third, two positive sputum smears with clinical signs and symptoms compatible with tuberculosis or a chest roentgenogram compatible with active pulmonary tuberculosis. For each progressor, 3 controls were matched according to recruitment region, age category (≤18, 19-25, 26-35, ≥36 years), gender and year of enrolment.

Participants with diagnosed or suspected tuberculosis disease were referred to a study-independent public health physician for treatment according to national tuberculosis control programs of the country involved.
RNA Sequencing (RNA-Seq) Analysis of the ACS Training Set Prior to RNA-Seq, the ACS progressors and controls were randomly divided into training and test sets at a ratio of 3:1. The test set samples remained unprocessed until analysis of the training set was complete.

PAXgene® tubes from the ACS training set were thawed and RNA was extracted with PAXgene® Blood RNA kits (QIAgen). RNA quality and quantity was assessed using RNA6000 Pico kits on a 2100 BioAnalyzer (Agilent). RNA samples with a RNA Integrity Number (RIN)≥7.0 were selected for RNA sequencing. Globin transcript depletion (GlobinClear, Life Technologies) was followed by cDNA library preparation using Illumina (mRNA-Seq Sample Prep Kit according to the manufacturer's instructions). RNA sequencing was then performed by Expression Analysis, Inc. The sequencing strategy was 30 million 50 bp paired-end reads, and was performed on Illumina HiSeq-2000 sequencers. Read pairs were aligned to the hg19 human genome reference sequence using gsnap (Wu and Nacu 2010) which generated a table of splice junction counts for each sample.
Construction of Signatures of Risk, Using RNA-Seq Data from the ACS Training Set A novel computational approach was developed to generate pair-wise support-vector machine ensemble models (PSVM) that predict tuberculosis disease risk based on gene product splice junction counts measured by RNA-Seq. Use of splice junction count data permitted seamless translation from RNA-Seq (Junction PSVM.1) to qRT-PCR (PCR PSVM.1), used in later analysis. A collection-based modelling approach was employed because these models are robust regardless of missing measurements, and guard against overfitting of the data. Prediction performance of the Junction PSVM.1 approach was assessed on the ACS training set by 100 iterations of cross-validation (CV) involving 4:1 splits. To ensure unbiased estimates of prediction accuracy, all junction selection, pair selection, and parameterization were performed inside of the CV loop. After confirmation of significant prediction performance by CV, the final PSVM.1 signature was generated by applying the algorithms to the entire ACS training set.

The prediction performance of PSVM.1 was also determined according to time before diagnosis in progressors, by integrating diagnosis or treatment initiation dates with study enrolment and blood draw dates. Two time to diagnosis values were calculated for each progressor. First, intent to treat (ITT) values were assigned early after sample collection and were employed throughout signature construction. Second, per protocol (PP) values were assigned during manuscript preparation when it was revealed that some ITT time to diagnosis assignments had been wrong. All prediction results (below) are reported in terms of PP values.

Splice junction counts for each sample were first pre-normalised for library size by adding "1" to the raw counts, dividing the counts in a given sample by the sum of all counts in that sample, and then taking the logarithm (base 2). "Reference junctions" for use as internal controls in all subsequent analyses were then identified from the 20 splice junctions with the smallest coefficient of variance computed across all samples from the pre-normalised table. The final normalised log 2-based splice junction table was finally constructed by subtracting the mean of the reference junction counts for each sample. Reference junctions were identified by using the 264 samples that comprise the full ACS training set RNA-Seq sample set, which included a small number of samples that were collected after the initiation of treatment. The set of reference gene products and junctions is provided in Table 8. The set of primers to detect reference gene products for (PCR PSVM.1) is provided in Table 9.

Quantitative Real Time PCR (qRT-PCR) Analysis of the ACS Training Set

The JunctionPSVM.1 signature was adapted from the original RNA-Seq-based platform to qRT-PCR (PCR PSVM.1) to allow affordable measurement on a large number of samples. Splice junctions in the models were first matched to commercial TaqMan primer sets (Thermo Fisher Scientific). Expression for all primers for the entire ACS training set was then measured using the BioMark HD instrument multiplex microfluidic instrument (Fluidigm). Normalisation of the cycle threshold data was performed by comparing expression of PSVM.1 gene products to a set of reference gene products. The PCR PSVM.1 signature was finally generated by re-training the pairwise SVM models to the normalised Ct data using the network structure obtained from RNA-Seq. Computational scripts that automatically import and normalise the raw Ct data and make predictions were constructed.

Blind Prediction on the ACS Test Set Using Junction-PSVM.1 and PCR PSVM.1 Signatures of Risk Trained on the ACS Training Set After the final JunctionPSVM.1 and PCR PSVM.1_signatures of risk were defined, RNA was extracted, in a blinded manner, from the ACS test set PAXgene tubes, as described above. These RNA samples were then analyzed by both RNA-Seq and qRT-PCR to generate fully blinded datasets that were compatible with JunctionPSVM.1 and PCR PSVM.1_versions of the signatures. Blind prediction of tuberculosis disease risk on both datasets was performed simultaneously, and both datasets were unblinded simultaneously.

Blind Prediction on the GC6-74 Validation Cohort Using qRT-PCR-Based Signatures of Risk Trained on the ACS Training Set After validation of the signatures of risk on the ACS test set, qRT-PCR data for the PCR PSVM.1 primers and reference gene products was generated from GC6-74 cohort RNA, in a blinded manner, as described above. Prior to predicting on GC6-74 RNA samples, two modifications to PCR PSVM.1 were made. First, failure of one reference primer (GRK6) on the GC6-74 samples necessitated exclusion of this primer and re-parameterization of the signatures (using ACS training set data only). Second, post-hoc inspection of PSVM.1 predictions on the ACS test set identified a subset of SVM pairs that always voted progressor or always voted control, irrespective of the sample. These pairs were pruned from the networks prior to predicting on GC6-74. Blind predictions were performed on the GC6-74 validation set using computational scripts that were locked down and distributed amongst collaborating sites prior to unblinding.

Construction of Signatures of Risk, Using RNA-Seq Data from the Full ACS Set

After blind predictions were made on the ACS test set using models trained on the ACS training set, the ACS training and test sets were combined into the full ACS set. The full ACS set was used to generate a small additional pair-wise ensemble model that predicts tuberculosis disease risk based on PCR amplification products.

Quantitative Real Time PCR (qRT-PCR) Analysis of the Full ACS Set

An additional, highly parsimonious PCR-specific model was developed that predicts solely on the basis of raw Ct counts and does not need reference primers in order to make predictions on novel samples. This small signature, which is based on 6 transcripts only, is referred to as PCR 6-gene. The PCR 6-gene signature was constructed by identifying pairs of primers for which the relative ordering of expression of the two primers reverses between progressors and non-progressors (Table 6 and 7).

Blind Prediction on the GC6-74 Validation Cohort Using qRT-PCR-Based Signatures of Risk Trained on the Full ACS Set New blinded sample codes were generated for the GC6-74 samples, and the primers from the PCR 6-gene signature were run on the blinded GC6-74 samples. Blind predictions from the PCR 6-gene signature models were performed on the GC6-74 validation set using computational scripts that were locked down and distributed amongst collaborating sites prior to unblinding.

Results

Participants

Forty-six ACS participants with microbiologically confirmed tuberculosis were identified as progressors (FIG. 1A). Time to diagnosis values for prospective progressor samples ranged from 1-894 days. One hundred and seven controls who were infected with tuberculosis at enrollment, but who remained healthy during two years of follow up, were matched to progressors. Prior to analysis, progressors and controls were randomly partitioned into a training set of 37 progressors and 77 controls, and a test set of 9 progressors and 30 controls (FIG. 1A).

The participants of the GC6-74 study were household contacts of index cases with pulmonary tuberculosis disease. Two GC6-74 sites, South Africa and the Gambia, had sufficient numbers of progressors and controls to allow analysis. A total of 75 progressors and 300 controls were identified at the South African site while 33 progressors and 132 controls were identified at the Gambian site (FIG. 1B). Time to diagnosis values for prospective progressor samples from the GC6-74 cohort were comparable to those of the ACS (data not shown).

Figure 2:
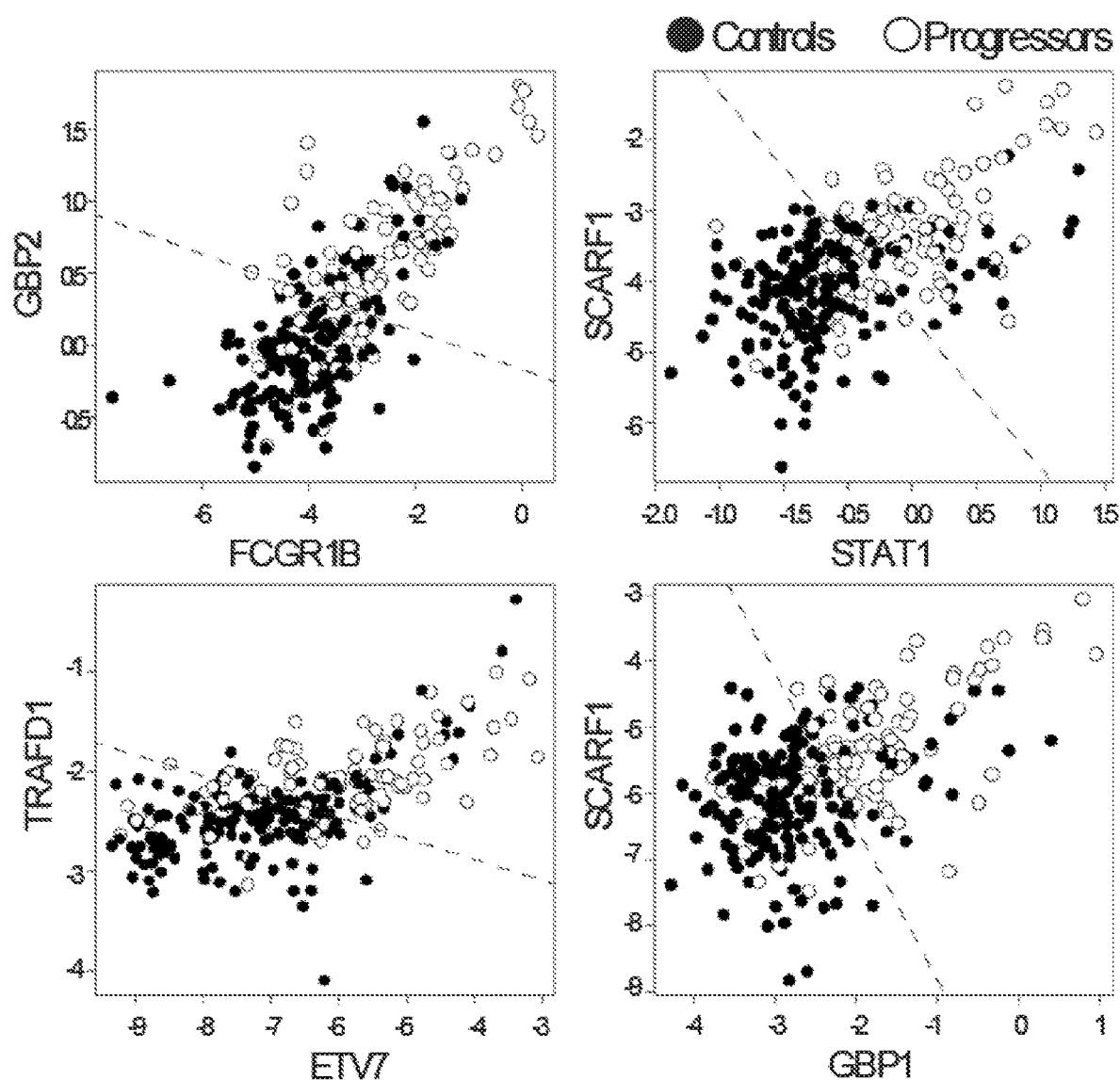
FIG. 2 shows representative junction-pair signatures that comprise the overall tuberculosis risk signature. In each scatterplot, the normalised expression of one gene product within the pair is plotted against the other for all ACS training data points (closed circles=control samples; open circles=progressor samples). The dotted black line indicates the optimal linear decision boundary for discriminating progressors from controls.
Figure 3:
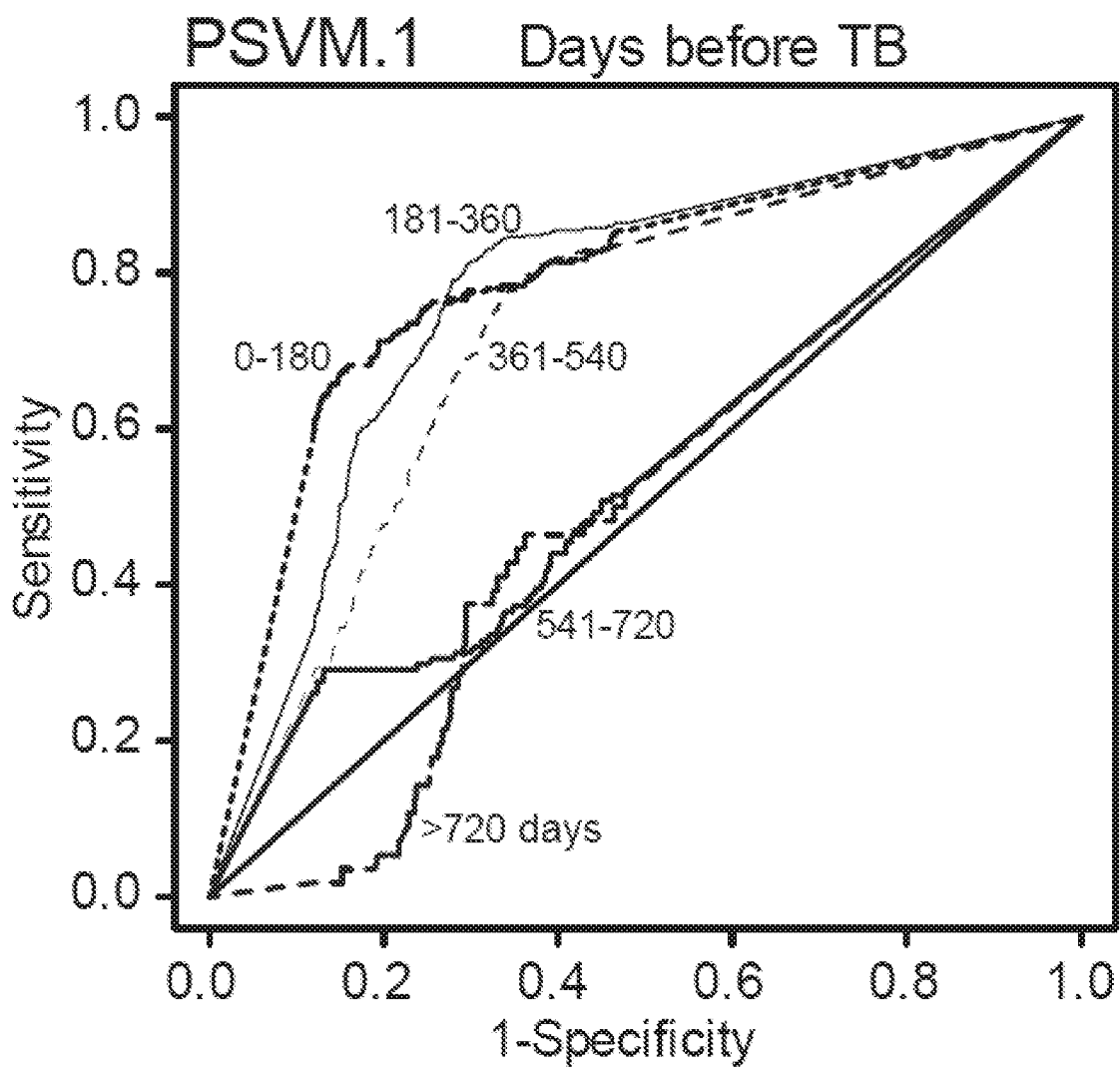
FIG. 3 shows receiver operating characteristic curves (ROCs) depicting the predictive potential of the tuberculosis risk signature for discriminating progressors from controls. Each ROC curve corresponds to a 180-day interval prior to tuberculosis diagnosis. Prediction performance was assessed by 100 four-to-one training-to-test splits of the ACS training set.

Construction of Blood Transcriptomic Signatures of Risk from the ACS Training Set RNA was isolated from progressor samples collected up to two and a half years prior to the diagnosis of active tuberculosis, and from matched controls, and analyzed by RNA-seq. The JunctionPSVM.1 signature is an ensemble of pair-wise models comprised of splice junctions from multiple gene products that exhibited differential expression between progressors and controls after normalisation by a set of reference gene products. Representative junction pairs are shown in FIG. 2. JunctionPSVM.1 consists of 258 SVM pairs (63 splice junctions derived from products of 16 unique genes). Cross validation analysis of the models illustrated ability to predict progression to active tuberculosis from prospectively collected samples (FIG. 3 and Table 10). JunctionPSVM.1 achieved 71.2% sensitivity in the 6 month period immediately prior to diagnosis, and 62.9% sensitivity 6-12 months before diagnosis. Prediction specificities of PSVM.1 was 80.6%. Appreciable prediction of active tuberculosis was observed up to 1½ years prior to diagnosis (PSVM.1 sensitivity was 47.7% in samples collected 12-18 months before diagnosis; FIG. 3).

Validation of the Signatures of Risk on the ACS Test Set

Prior to making predictions on the ACS test set, the signature was adapted to the qRT-PCR platform to facilitate wider application. A comparable fit of signatures using RNA-Seq and qRT-PCR data was shown (R>0.9). Blind predictions using RNA-seq and qRT-PCR versions of the signature were then made simultaneously on the ACS test set. The ability of both signatures to predict active tuberculosis was validated on the qRT-PCR platform (PCR PSVM.1: p=0.009; FIG. 3).

Validation of the Signatures of Risk on the Independent GC6-74 Cohort

For independent validation, we used the PCR PSVM.1 signature to make blind predictions of tuberculosis disease on prospective samples collected from the GC6-74 cohort. The signature validated in ability to predict active tuberculosis when the cohort was analyzed collectively (PCR PSVM.1: p=$4 \times 10^{-8}$), and when the South African and Gambian cohorts were analyzed independently (Table 10). The robustness of the signature for predicting tuberculosis progression was surprising given the geographic and genetic diversity of the two sites. As in the ACS, the signature had greater sensitivity for predicting tuberculosis from samples collected closer to the time of diagnosis.

We also used the qRT-PCR PCR 6-gene signature, derived from the full ACS set, to make blind predictions of tuberculosis disease on prospective samples collected from the GC6-74 cohort. This small signature validated in ability to predict active tuberculosis when the cohort was analyzed collectively (p=$2 \times 10^{-8}$), and when the South African and Gambian cohorts were analyzed independently (Table 10).

Prevention or Reduction of Incidence of Active TB and Reduction in TB Mortality

Drs Richard White and Tom Sumner at the London School of Hygiene and Tropical Medicine have performed epidemiological modeling to estimate the population-level impact of an annual screen and treat campaign, based on identification of persons at risk of TB using the prognostic correlate of risk method of the invention (results not shown).

A dynamic transmission model, calibrated to the South African TB epidemic, was used. In the first instance, they modeled the impact of annual screening of 30% of the adult HIV uninfected population only starting in the year 2020; and treating only those who were COR-positive with a regimen of 3 months of isozianid and rifapentine. The results show that a strategy which reached 30% of the adult HIV uninfected population per year could reduce TB incidence by 7% (6.2-8.4) after one year; and 13% (9.0-14.9) after 5 years, with corresponding reductions in mortality of 4% (3.5-4.7) and 14% (11.5-17.8) after 1 and 5 years, respectively. If extended to both HIV uninfected and HIV infected adults (and conservatively assuming COR sensitivity for predicting incident TB is reduced by 15% in HIV infected individuals), this single strategy is estimated to reduce TB incidence by 29% (24.0-31.5) and TB mortality by 35% (29.5-37.4) by 2025.

Discussion

Approximately one third of the world's population harbours latent tuberculosis infection and is at risk of active disease.

The applicants have demonstrated here, for the first time, that it is possible to predict progression from latent to active disease in asymptomatic, healthy persons, using transcriptomic signatures from peripheral blood. The transcriptomic signatures of risk of active tuberculosis were identified in a longitudinal study of South African adolescents with latent tuberculosis infection. These signatures were validated on a separate set of adolescents from the same parent cohort. The broad utility of the signatures was demonstrated by application to an independent cohort of longitudinally followed household contacts of patients with tuberculosis disease, from South Africa (SUN), the Gambia (MRC) and Ethiopia (AHRI).

To maximize our chances for discovering predictive signatures of tuberculosis disease risk, we used RNA-Seq for transcriptomic analysis, since this approach is quantitative, sensitive, and unbiased (Wang, Gerstein et al. 2009). However, because this technology cannot be optimized for use in the field, we developed computational approaches to biomarker discovery that allow seamless adaptation to technologies that are broadly applicable: we constructed the signatures in terms of the expression of splice junctions that were easily mapped to PCR primers. Also relevant to application in the field, where the possibility of incomplete data and failed reactions are high, we formulated the signatures as ensembles of small models that eliminated reliance on any single primer, resulting in robust tests.

The signatures predicted tuberculosis disease despite multiple confounders, including differences in age range (adolescents versus adults), in infection or exposure status, and in ethnicity and geography between the ACS and GC6-74 cohorts. This result is very encouraging given the distinct genetic backgrounds (Tishkoff, Reed et al. 2009), differing local epidemiology (WHO 2014), and differing circulating strains of Mycobacteria (Comas, Coscolla et al. 2013) between South Africa (SUN) and the Gambia (MRC).

Our predictive signatures were obtained from transcriptomic analysis of peripheral blood. This compartment, although conveniently sampled, may not accurately reflect the molecular mechanisms underlying the pathogenesis of tuberculosis in the lung. Despite this shortcoming, circulating white blood cells serve as sentinels in that they sample the environment through which they traverse and undergo transcriptional changes that are indicative of the disease process within the organ of interest, in this case the lung.

Our results demonstrating that blood-based signatures in healthy individuals can predict progression to active tuberculosis disease has paved the way for the establishment of devices that are scalable and inexpensive and that can exploit the signatures within the blood for diagnostic purposes. In addition, these newly described signatures hold the potential for highly targeted preventive therapy, and therefore for interrupting the global epidemic.

Modeling studies performed have shown that it is likely that a strategy whereby 30% of the adult HIV uninfected population are screened each year with the prognostic correlate of risk method of the invention, followed by treatment of COR-positive subjects with a regimen of 3 months of isozianid and rifapentine, could reduce TB incidence by up to 13% (9.0-14.9) after 5 years, with corresponding reductions in mortality of up to 14% (11.5-17.8) and that similarly in HIV infected adults the TB incidence could be reduced by 29% (24.0-31.5) and TB mortality by 35% (29.5-37.4) by 2025.

REFERENCES

Anderson, S. T., M. Kaforou, A. J. Brent, V. J. Wright, C. M. Banwell, G. Chagaluka, A. C. Crampin, H. M. Dockrell, N. French, M. S. Hamilton, M. L. Hibberd, F. Kern, P. R. Langford, L. Ling, R. Mlotha, T. H. Ottenhoff, S. Pienaar, V. Pillay, J. A. Scott, H. Twahir, R. J. Wilkinson, L. J. Coin, R. S. Heyderman, M. Levin, B. Eley, I. Consortium and K. T. S. Group (2014). "Diagnosis of childhood tuberculosis and host RNA expression in Africa." N Engl J Med 370(18): 1712-1723.

Berry, M. P., C. M. Graham, F. W. McNab, Z. Xu, S. A. Bloch, T. Oni, K. A. Wilkinson, R. Banchereau, J. Skinner, R. J. Wilkinson, C. Quinn, D. Blankenship, R. Dhawan, J. J. Cush, A. Mejias, O. Ramilo, O. M. Kon, V. Pascual, J. Banchereau, D. Chaussabel and A. O'Garra (2010). "An interferon-inducible neutrophil-driven blood transcriptional signature in human tuberculosis." Nature 466(7309): 973-977.

Bloom, C. I., C. M. Graham, M. P. Berry, F. Rozakeas, P. S. Redford, Y. Wang, Z. Xu, K. A. Wilkinson, R. J. Wilkinson, Y. Kendrick, G. Devouassoux, T. Ferry, M. Miyara, D. Bouvry, D. Valeyre, G. Gorochov, D. Blankenship, M. Saadatian, P. Vanhems, H. Beynon, R. Vancheeswaran, M. Wickremasinghe, D. Chaussabel, J. Banchereau, V. Pascual, L. P. Ho, M. Lipman and A. O'Garra (2013). "Transcriptional blood signatures distinguish pulmonary tuberculosis, pulmonary sarcoidosis, pneumonias and lung cancers." PLoS One 8(8): e70630.

Bloom, C. I., C. M. Graham, M. P. Berry, K. A. Wilkinson, T. Oni, F. Rozakeas, Z. Xu, J. Rossello-Urgell, D. Chaussabel, J. Banchereau, V. Pascual, M. Lipman, R. J. Wilkinson and A. O'Garra (2012). "Detectable changes in the blood transcriptome are present after two weeks of antituberculosis therapy." PLoS One 7(10): e46191.

Comas, I., M. Coscolla, T. Luo, S. Borrell, K. E. Holt, M. Kato-Maeda, J. Parkhill, B. Malla, S. Berg, G. Thwaites, D. Yeboah-Manu, G. Bothamley, J. Mei, L. Wei, S. Bentley, S. R. Harris, S. Niemann, R. Diel, A. Aseffa, Q. Gao, D. Young and S. Gagneux (2013). "Out-of-Africa migration and Neolithic coexpansion of Mycobacterium tuberculosis with modern humans." Nat Genet 45(10): 1176-1182.

Kaforou, M., V. J. Wright, T. Oni, N. French, S. T. Anderson, N. Bangani, C. M. Banwell, A. J. Brent, A. C. Crampin, H. M. Dockrell, B. Eley, R. S. Heyderman, M. L. Hibberd, F. Kern, P. R. Langford, L. Ling, M. Mendelson, T. H. Ottenhoff, F. Zgambo, R. J. Wilkinson, L. J. Coin and M. Levin (2013). "Detection of tuberculosis in HIV-infected and *uninfected African adults using whole blood RNA expression signatures: a case-control study." PLoS Med 10(10): e1001538.

Maertzdorf, J., M. Ota, D. Repsilber, H. J. Mollenkopf, J. Weiner, P. C. Hill and S. H. Kaufmann (2011). "Functional correlations of pathogenesis-driven gene expression signatures in tuberculosis." PLoS One 6(10): e26938.

Maertzdorf, J., D. Repsilber, S. K. Parida, K. Stanley, T. Roberts, G. Black, G. Walzl and S. H. Kaufmann (2011). "Human gene expression profiles of susceptibility and resistance in tuberculosis." Genes Immun 12(1): 15-22.

Maertzdorf, J., J. Weiner, 3rd, H. J. Mollenkopf, T. B. Network, T. Bauer, A. Prasse, J. Muller-Quernheim and S. H. Kaufmann (2012). "Common patterns and disease-related signatures in tuberculosis and sarcoidosis." Proc Natl Acad Sci USA 109(20): 7853-7858.

Mahomed, H., R. Ehrlich, T. Hawkridge, M. Hatherill, L. Geiter, F. Kafaar, D. A. Abrahams, H. Mulenga, M. Tameris, H. Geldenhuys, W. A. Hanekom, S. Verver and G. D. Hussey (2013). "TB incidence in an adolescent cohort in South Africa." PLoS One 8(3): e59652.

Mahomed, H., T. Hawkridge, S. Verver, D. Abrahams, L. Geiter, M. Hatherill, R. Ehrlich, W. A. Hanekom and G. D. Hussey (2011). "The tuberculin skin test versus QuantiFERON TB Gold® in predicting tuberculosis disease in an adolescent cohort study in South Africa." PLoS One 6(3): e17984.

Ottenhoff, T. H., R. H. Dass, N. Yang, M. M. Zhang, H. E. Wong, E. Sahiratmadja, C. C. Khor, B. Alisjahbana, R. van Crevel, S. Marzuki, M. Seielstad, E. van de Vosse and M. L. Hibberd (2012). "Genome-wide expression profiling identifies type 1 interferon response pathways in active tuberculosis." PLoS One 7(9): e45839.

Owzar, K., W. T. Barry and S. H. Jung (2011). "Statistical considerations for analysis of microarray experiments." Clin Transl Sci 4(6): 466-477.

Platt, J. C. (1998). "Sequential Minimal Optimization: A Fast Algorithm for Training Support Vector Machines." Microsoft Research Technical Report MSR-TR-98-14.

Sambrook, J., D. W. Russell and J. Sambrook (2006). The condensed protocols from Molecular cloning: a laboratory manual. Cold Spring Harbor, N.Y., Cold Spring Harbor Laboratory Press.

Shi, P., S. Ray, Q. Zhu and M. A. Kon (2011). "Top scoring pairs for feature selection in machine learning and applications to cancer outcome prediction." BMC Bioinformatics 12: 375.

Sutherland, J. S., A. G. Loxton, M. C. Haks, D. Kassa, L. Ambrose, J. S. Lee, L. Ran, D. van Baarle, J. Maertzdorf, R. Howe, H. Mayanja-Kizza, W. H. Boom, B. A. Thiel, A. C. Crampin, W. Hanekom, M. O. Ota, H. Dockrell, G. Walzl, S. H. Kaufmann, T. H. Ottenhoff and G. B. f. T. consortium (2014). "Differential gene expression of activating Fcgamma receptor classifies active tuberculosis regardless of hum an immunodeficiency virus status or ethnicity." Clin Microbiol Infect 20(4): O230-238.

Tishkoff, S. A., F. A. Reed, F. R. Friedlaender, C. Ehret, A. Ranciaro, A. Froment, J. B. Hirbo, A. A. Awomoyi, J. M. Bodo, O. Doumbo, M. Ibrahim, A. T. Juma, M. J. Kotze, G. Lema, J. H. Moore, H. Mortensen, T. B. Nyambo, S. A. Omar, K. Powell, G. S. Pretorius, M. W. Smith, M. A. Thera, C. Wambebe, J. L. Weber and S. M. Williams (2009). "The genetic structure and history of Africans and African Americans." Science 324(5930): 1035-1044.

Wang, Z., M. Gerstein and M. Snyder (2009). "RNA-Seq: a revolutionary tool for transcriptomics." Nat Rev Genet 10(1): 57-63.

WHO, W. H. O. (2014) "Global Tuberculosis Report 2014.".

The invention claimed is:

1. A kit comprising:
  (a) 6 sets of primers and/or 6 sets of oligonucleotide probes configured to amplify and/or bind to 9 pairs of gene products of the following 6 human genes: GBP2, FCGR1 B, SERPING1, TUBGCP6, TRMT2A, and SDR39U1, the 9 pairs of gene products consisting of:
    aa. GBP2 and TUBGCP6;
    bb. GBP2 and TRMT2A;
    cc. GBP2 and SDR39U1;
    dd. FCGR1B and TUBGCP6;
    ee. FCGR1B and TRMT2A;
    ff. FCGR1B and SDR39U1;
    gg. SERPING1 and TUBGCP6;
    hh. SERPING1 and TRMT2A; and
    ii. SERPING1 and SDR39U1; and
  (b) instructions for performing a method for determining the risk of a human subject with asymptomatic TB infection or suspected TB infection progressing to active tuberculosis disease, wherein the instructions include:
    (i) obtaining a sample from a human subject with asymptomatic TB infection or suspected TB infection;
    (ii) quantifying and computationally analysing relative abundances of the 9 pairs of gene products (TB biomarkers); and
    (iii) computing a prognostic score of the risk of the subject developing active TB disease based on the relative abundance of the 9 pairs of gene products, thus classifying the subject as "progressor" or "control", wherein a prognostic score of "progressor" indicates that the subject with asymptomatic TB infection or suspected TB infection is likely to progress to active TB disease.

2. The kit according to claim 1, which further comprises reference primers and/or oligonucleotide probes configured to amplify and/or bind to a collection of gene products of genes selected from the group consisting of ACTR3, ADRBK1, CDC42, CSDE1, CYTIP, TMBIM6, TPM3, and USF2 for computing a sample-specific normalisation factor for normalising the relative abundances quantified prior to mathematically associating the quantified abundances.

* * * * *